US006355161B1

(12) United States Patent
Shah et al.

(10) Patent No.: US 6,355,161 B1
(45) Date of Patent: Mar. 12, 2002

(54) BOTTLES FOR DIALYSIS MACHINES AND METHOD FOR AUTOMATICALLY IDENTIFYING SUCH BOTTLES

(75) Inventors: Dilip H. Shah, Buffalo Grove, IL (US); Gary Howell, Elkton, MD (US); Kenneth E. Pawlak, Vernon Hills, IL (US); Masatoshi Ozono, Tokyo (JP); Wade Fournier, Spring Grove; Mete Alpan, LaGrange, both of IL (US)

(73) Assignees: Aksys, Ltd., Lincolnshire, IL (US); Teijin, Ltd., Osaka (JP)

( * ) Notice: Subject to any disclaimer, the term of this patent is extended or adjusted under 35 U.S.C. 154(b) by 0 days.

(21) Appl. No.: 09/549,897

(22) Filed: Apr. 14, 2000

Related U.S. Application Data

(63) Continuation-in-part of application No. 29/112,243, filed on Oct. 12, 1999, now Pat. No. Des. 435,646, and a continuation-in-part of application No. 29/112,244, filed on Oct. 12, 1999, now Pat. No. Des. 435,647, and a continuation-in-part of application No. 29/112,249, filed on Oct. 12, 1999, now Pat. No. Des. 435,648, and a continuation-in-part of application No. 29/112,250, filed on Oct. 12, 1999, now Pat. No. Des. 435,649.

(51) Int. Cl.[7] ............................ B01D 61/28; B01D 61/30

(52) U.S. Cl. .................. 210/91; 210/321.71; 210/647; 206/570; 206/459.1; 206/459.5; 215/382; 220/669

(58) Field of Search .......................... 210/321.71, 541, 210/646, 647, 91, 94; 215/365, 382–384, DIG. 3; 206/223, 570, 568, 459.1, 459.5, 483; 220/669; 604/4.01, 5.01, 6.01, 6.09

(56) References Cited

U.S. PATENT DOCUMENTS 4,197,942 A    4/1980  Gacki et al. ............... 206/219

4,247,001 A           1/1981  Wiegner
4,379,099 A    *      4/1983  Ota et al.
RE31,496 E    *      1/1984  Keeler
5,178,920 A    *      1/1993  Ota et al.
5,239,491 A           8/1993  Mucciacciaro (List continued on next page.)

FOREIGN PATENT DOCUMENTS

DE      19814687      2/1999
EP      0341799       5/1989

OTHER PUBLICATIONS

PCT International Search Report for International Application No. PCT/US01/03144 for Aksys, Ltd. et al., dated Jan. 31, 2001.

Primary Examiner—Joseph W. Drodge
(74) Attorney, Agent, or Firm—McDonnell Boehnen Hulbert & Berghoff

(57) ABSTRACT

A set of bottles for containing dialysate chemical formulations, chemical cleaning agents or the like is described. The chemical formulation bottles come in two varieties, sodium bicarbonate and liquid acid formulations, each bottle having a slightly different shape. The different shapes cooperate with a bottle mounting structure in the dialysis machine to insure that bottles are correctly installed on their respective bottle opening mechanism. The bottles also have a detection feature comprising either a raised rim or groove extending around the periphery of the bottle. A sensor assembly in the bottle mounting and opening system detects the detection feature. The detection feature is used by the machine to distinguish between dialysate formulation bottles and chemical cleaning bottles, which do not have the detection feature. The detection feature prevents unintentional installation of the chemical bottle on the opening mechanism for the dialysate chemical formulation bottles. A chemical loading system for use with the bottles, and having a detection system for detecting the detection feature is also described. The detection system can be either a mechanical detection system or an optical detection system.

52 Claims, 16 Drawing Sheets

U.S. PATENT DOCUMENTS

| | | |
|---|---|---|
| 5,326,473 A | 7/1994 | Lacombes .................... 210/474 |
| 5,336,165 A | 8/1994 | Twardowski ............... 604/4.01 |
| D358,219 S | 5/1995 | Ushikubo .................. D24/224 |
| 5,487,827 A | 1/1996 | Peterson et al. .............. 210/87 |
| 5,547,645 A | 8/1996 | Ego et al. .................... 422/204 |
| D374,481 S | 10/1996 | McCallister et al. ........ D24/121 |
| D376,424 S | 12/1996 | Macauley .................. D24/121 |
| 5,591,344 A | 1/1997 | Kenley et al. ............... 210/636 |
| 5,658,456 A | 8/1997 | Kenley et al. ................ 210/85 |
| 5,714,060 A | 2/1998 | Kenley et al. ............... 210/194 |
| 5,717,217 A * | 2/1998 | Anderson et al. |
| D395,517 S | 6/1998 | Treu et al. .................. D24/224 |
| 5,788,099 A | 8/1998 | Treu et al. ................... 215/230 |
| D403,079 S | 12/1998 | Pawlak ....................... D24/224 |
| 5,932,110 A | 8/1999 | Shah et al. ................... 210/739 |
| 6,036,858 A | 3/2000 | Carlsson et al. ............ 210/232 |
| D435,646 S | 12/2000 | Shah et al. ................. D24/108 |
| D435,647 S | 12/2000 | Shah et al. ................. D24/108 |
| D435,648 S | 12/2000 | Shah et al. ................. D24/108 |
| D435,649 S | 12/2000 | Shah et al. ................. D24/108 |

* cited by examiner

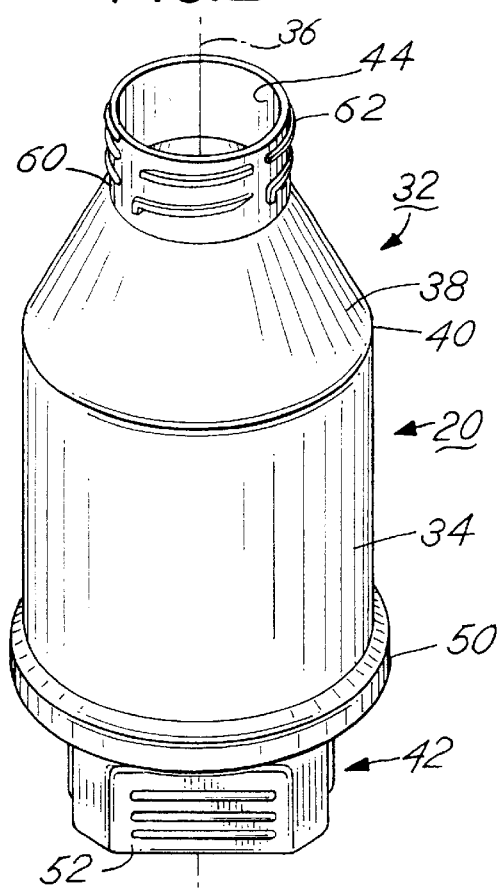
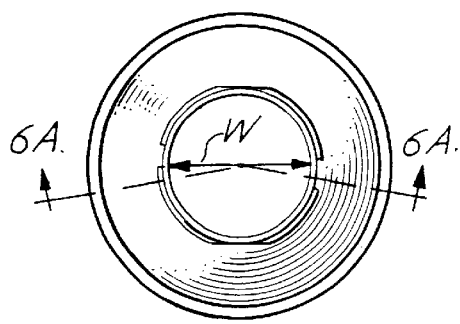
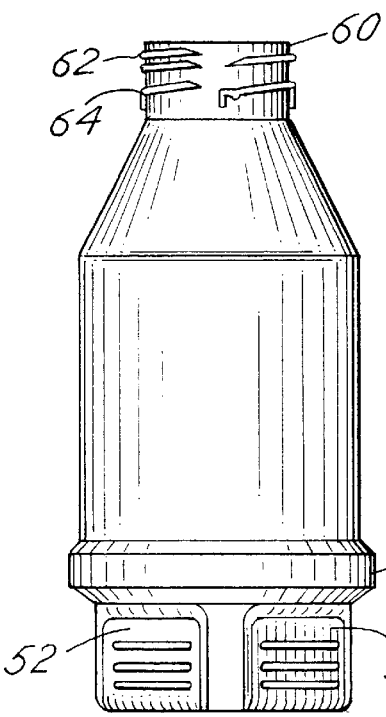
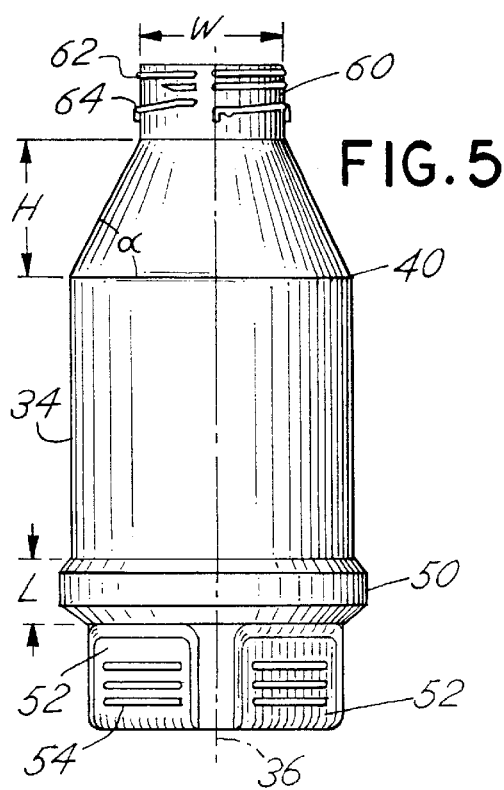
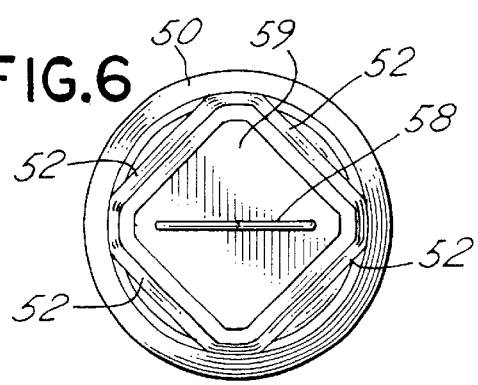

FIG.12
FIG.13
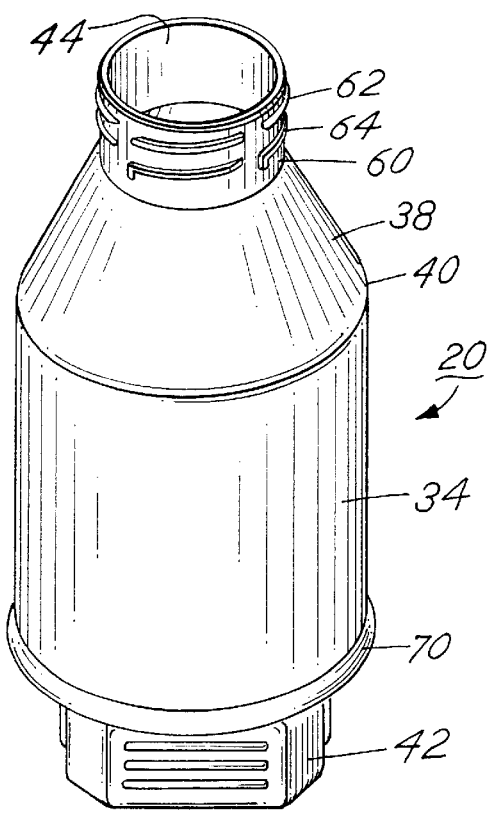
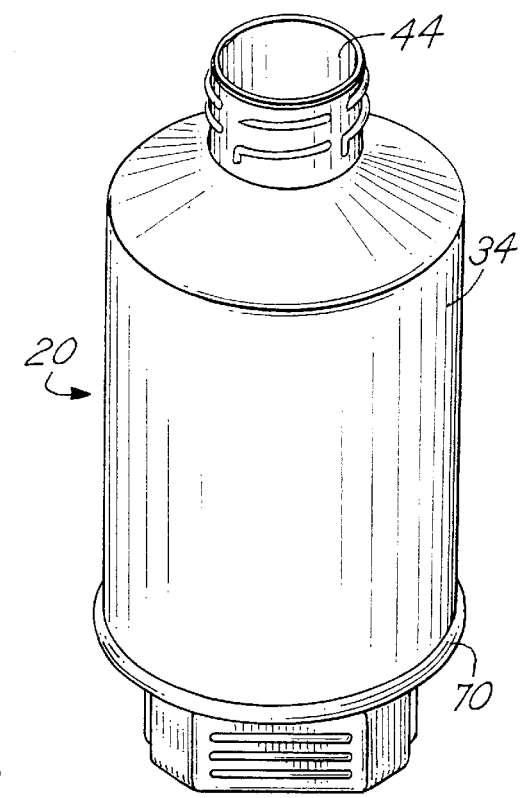
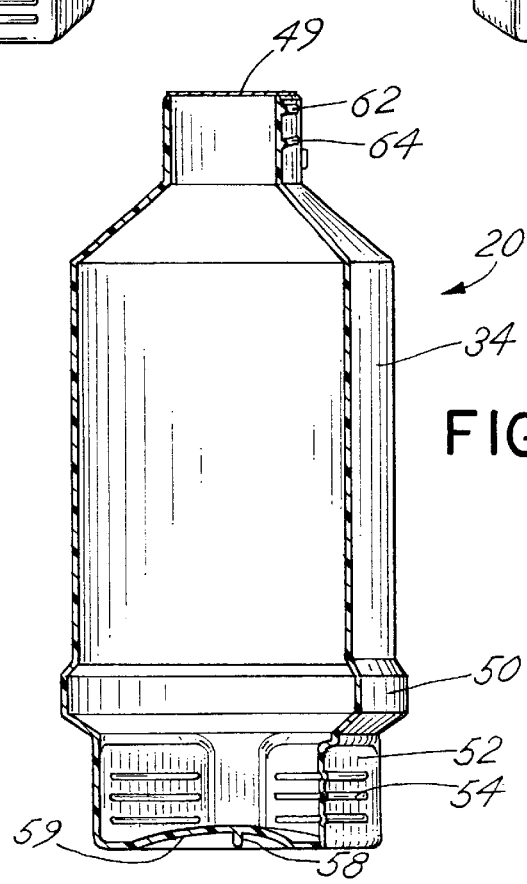
FIG.6A

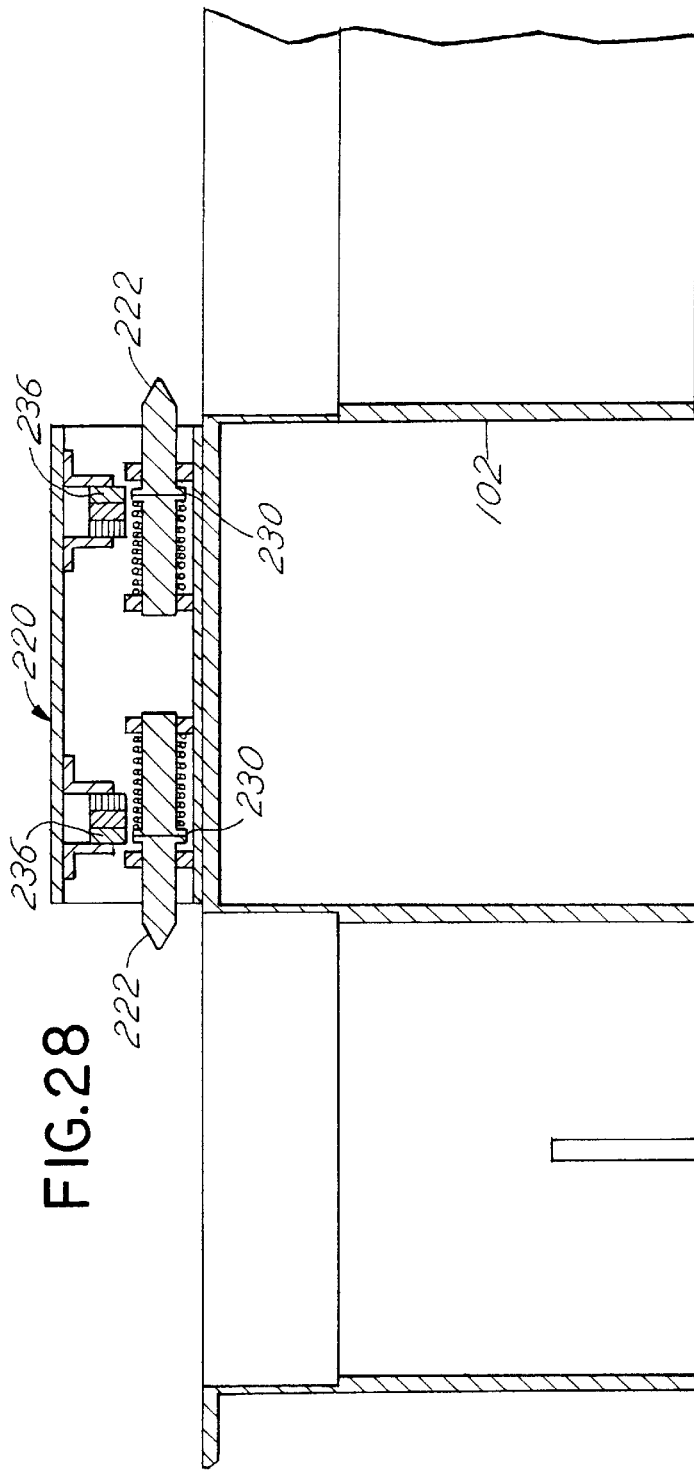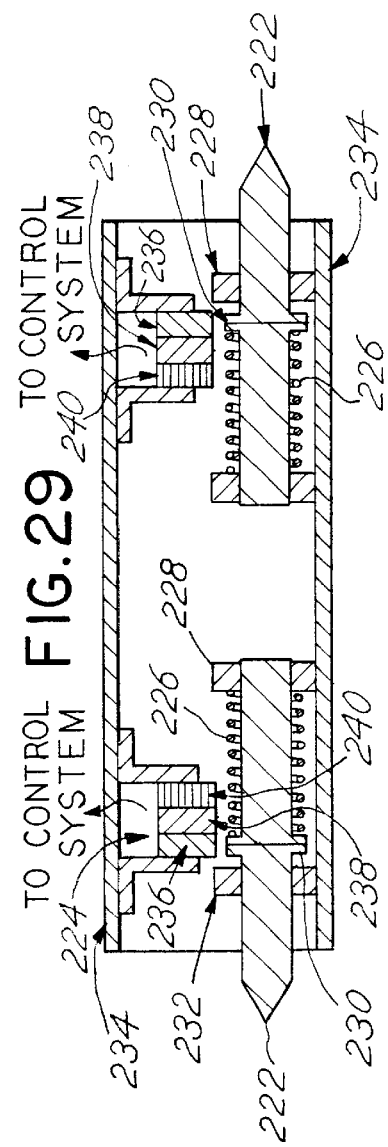

BOTTLES FOR DIALYSIS MACHINES AND METHOD FOR AUTOMATICALLY IDENTIFYING SUCH BOTTLES

CROSS-REFERENCE TO RELATED APPLICATIONS

This is a continuation in part of four U.S. Design patent applications filed by the present inventors on Oct. 12, 1999, Ser. No. 29/112,243 now U.S. Design Pat. No. D,435,646; Ser. No. 29/112,244 now U.S. Design Pat. No. D,435,647; Ser. No. 29/112,249 now Design Pat. No. D,435,648; and 29/112,250 now Design Pat. No. D,435,649.

BACKGROUND OF THE INVENTION

A. Field of the Invention

This invention relates generally to the field of dialysis and machines for performing dialysis therapy. More particularly, the invention relates to a bottle for containing dialysate chemicals, cleaning agents, or other substances that may be introduced in a dialysis machine treating a dialysis patient. The invention also relates to a chemical loading system and method for distinguishing different types of bottles from each other.

B. Related Art

Dialysis is a treatment for persons suffering from inadequate kidney function. A dialysis machine is an artificial kidney machine that treats the blood of a dialysis patient. Dialysis machines typically incorporate an extracorporeal blood circuit having a semipermeable dialyzer membrane. During dialysis therapy, blood from the patient is circulated through the extracorporeal circuit to the dialyzer membrane, where toxins and excess water are transported through the dialyzer membrane into a dialysate solution. The treated blood is then returned to the patient.

Dialysis machines also typically include a dialysate preparation system. This system prepares a dialysate solution by mixing concentrated chemicals (typically a mixture of sodium bicarbonate, an acid, solution, and additional minerals and salts) with reverse-osmosis filtered water.

Dialysate preparation systems come in two varieties, proportioning systems and batch systems. In proportioning systems, the concentrated dialysate chemicals are proportioned with water to provide a continuous supply of dialysis solution to the dialyzer. A representative proportioning system is described in Peterson et al., U.S. Pat. No. 5,487,827. In a batch system, an entire batch of dialysate solution is made in advance of the patient connecting to a dialysis machine. The batch of dialysate solution is typically made in the dialysis machine from a mixture of a batch quantity of dialysate solution chemicals and a large volume (e.g., 50 liters) of water. Representative patents describing batch systems are Twardowski, U.S. Pat. No. 5,336,165, and Kenley et al., U.S. Pat. No. 5,591,344. The entire contents of the Twardowski '165 and Kenley et al. '344 patents are incorporated by reference herein.

With a batch dialysate preparation system, the amount of dialysate solution chemicals needed to prepare a batch of dialysate solution is preferably measured out and packaged in a vessel, and the vessel shipped to the location where the machine is located. Typically, as taught in Kenley et al., the chemicals will include one vessel containing a liquid acid formulation and another vessel containing a powdered sodium bicarbonate formulation. This format for providing batch chemicals measured into batch chemical vessel bottles allows for careful control over the quantity of chemicals and the formulation, thereby promoting patient safety. The ready-to-use batch quantity bottles are also convenient for the user of the machine.

There are several technical problems in designing a suitable vessel for containing batch quantity dialysate chemical formulations. This is particularly the case where the bottles and dialysis machine may be used outside of a conventional dialysis clinic, such as in a home or nursing home environment. One challenge is to design the bottle and machine in a manner to minimize or eliminate the risk that the user of the machine may inadvertently install the wrong bottles on the machine (such as two liquid acid bottles instead of one acid and one bicarbonate). Another difficulty is designing the bottle so that the contents may be readily dispersed into the dialysate preparation system automatically, reasonably quickly, and without human intervention. This is particularly the case with a powdered bicarbonate chemical formulation, which has a tendency to clump if the vessel is exposed to heat such as may occur during shipping or storage, or if the bottle is exposed to hot water during a heat disinfection process.

Patents describing bottles specifically designed for containing batch quantities of dialysate solution chemicals include the above-referenced Kenley et al. '344 patent, U.S. Design Pat. No. D 395,517; U.S. Pat. No. 5,788,099 and U.S. Design Pat. No. D 403,079, each of which is assigned to Aksys Ltd.

The present inventive bottle provides features that ensure that only the correct combination of bottles can be installed in the dialysis machine. Further, the bottle includes features that promote the removal of substantially all the contents of the bottle by a bottle opening mechanism in the dialysis machine. These and still other features of the bottle will be described in the following detailed description of the preferred embodiment of the invention.

SUMMARY OF THE INVENTION

In a first aspect, a bottle is provided for containing chemicals to be introduced into a dialysis machine. The bottle is adapted to be installed in a chemical loading system in the dialysis machine which opens the bottle and introduces the chemicals into a fluid path in the dialysis machine. The bottle comprises a cylindrical bottle shell having a sidewall defining a bottle axis, a shoulder portion, a corner portion at which the shoulder portion intersects the sidewall, a lower portion, and a mouth through which the chemicals may be withdrawn from the bottle. The bottle further comprises a detection feature, such as either at least one raised rim extending outwardly from the sidewall extending around the circumference of the sidewall in a manner perpendicular to the axis of the bottle, or a circumferential groove or indentation extending inwardly form the sidewall in a manner perpendicular to the bottle axis. The raised rim or, alternatively, groove, is positioned on the sidewall a predetermined distance from the corner portion of the bottle and the mouth of the bottle. When the bottle is installed on the chemical loading system, the rim or groove of the bottle is detected by a detection system in the chemical loading system. For example, optical or mechanical detectors may be positioned in the chemical loading system to detect the presence of the rim or groove of the bottle.

As will be explained below, the bottle may contain a powdered dialysate chemical formulation or a liquid acid formulation. A second type of bottle that does not have the raised rim or groove (i.e., the bottle sidewall is smooth) may be provided, which contains cleaning or disinfection chemicals. When the second type of bottle is installed on the chemical loading system, the absence of the rim or groove will be detected by the detection system. Thus, the system can differentiate between the bottles containing chemical cleaning agents and dialysate chemicals.

The detection of the rim of groove by the detection system will allow the control system to distinguish the contents of the bottles. For example, bottles having cleaning compositions may have a raised rim detection feature, whereas the bottles having powdered bicarbonate formulations may have a groove feature. This type of system is a simple and reliable way to automate the detection of the bottles in the chemical loading system, while distinguishing between different types of bottles that may be installed in the chemical loading system.

In another aspect of the invention, the liquid acid and bicarbonate formulations are stored in two different bottles. Both bottles have at least one raised rim (or, alternatively, indentation or groove) extending outwardly from the sidewall extending around the circumference of the sidewall in a manner perpendicular to the axis of the bottle, with the raised rim positioned on the sidewall a predetermined distance from the corner portion of the bottle and the mouth of the bottle. However, the shoulder and mouth of the two bottles are given a different configuration. The shoulder and mouth of the bicarbonate formulation bottle is given a configuration that promotes ready release of a powdered composition, such as a steeper shoulder configuration and a wider mouth.

In another aspect, the chemical loading system may contain two different chemical loading mechanisms. One mechanism is particularly designed and adapted to receive the bottle containing the bicarbonate formulation. The other mechanism is particularly designed and adapted to receive the bottle containing the liquid acid formulation. If the user inadvertently attempts to install the bottle containing the liquid acid formulation in the chemical loading mechanism for the bicarbonate formulation bottle, a mismatch or interference occurs. Similarly, if the user attempts to install the bottle containing the bicarbonate formulation on the liquid acid loading mechanism, a mismatch or interference occurs. This design provides a fool-proof way of insuring that the user can only install the bicarbonate and liquid acid formulation bottles on the correct chemical loading mechanisms.

In yet another aspect, the shoulder portion of the bottle comprises a frusto-conical wall having a cone angle that is optimized for dispersion of the contents of the bottle. For example, if the bottle contains a powdered bicarbonate formulation, the cone angle may between 60 and 70 degrees. If the bottle contains a liquid acid formulation, the cone angle may be lesser, such as between about 30 degrees and about 40 degrees. The frusto-conical wall is also given a predetermined height, and the mouth is given a diameter such as between 1 and 2 inches.

The neck portion of the bottle includes a set of bayonet screw threads adapted for mounting the bottle to the bottle opening mechanism. A second set of screw threads is also included in the neck. The second set of screw threads receives a cap providing protection for a heat-sealed membrane covering the top of the bottle. The bayonet screw threads will not engage the chemical loading system unless the cap has been first removed from the bottle.

In yet another aspect, the present invention provides a kit for preparation of a batch of dialysate solution in a dialysis machine. The kit includes a bicarbonate formulation contained in a first batch chemical vessel and a liquid acid formulation contained in a second batch chemical vessel. The first and second batch chemical vessels comprises a cylindrical sidewall defining a bottle axis, a shoulder portion, a corner portion at which the shoulder portion intersects the sidewall, a lower portion, and a mouth through which the chemicals may be withdrawn from the bottle. The shoulder portion of the first batch chemical vessel comprises a frusto-conical wall having a first cone angle and a first height, and wherein the mouth has first diameter. The shoulder portion of the second batch chemical vessel also comprises a frusto-conical wall, but the cone angle is different from cone angle of the first bottle. The height of the shoulder of the second bottle is also different from the height of the shoulder of the first bottle. Further, the mouth of the second vessel has a second diameter different from the diameter of the first vessel. These differences in cone angle, shoulder height, and mouth diameter cooperate with first and second bottle mounting structures adapted to receive the first and second bottles, respectively, in the dialysis machine to thereby prevent the first and second bottles from being inadvertently installed on the second and first bottle mounting structures, respectively.

In another aspect of the invention, a chemical loading system is provided which comprises optical or mechanical detectors for detecting the presence of a physical configuration on the exterior of the bottle (e.g., raised rim or goove) to discriminate between two different types of bottles. The detection system can be either an optical detection system or a mechanical detection system.

Further aspects and features of the present invention will be more apparent from the following detailed description and the appended drawing figures.

BRIEF DESCRIPTION OF THE DRAWINGS

Presently preferred forms of the invention are depicted in the appended drawing figures, where like reference numerals refer to like elements in the various views and wherein:

FIG. 2 is a perspective view of a bottle particularly suitable for containing a batch quantity of dialysate chemicals, cleaning agents, or other substances in powdered form, designed to be introduced into the dialysis machine of FIG. 1;

FIG. 3 is a top plan view of the bottle of FIG. 2;

FIG. 4 is a side elevational view of the bottle of FIG. 2;

FIG. 5 is another side elevational view of the bottle of FIG. 2, with the bottle shown rotated 90 degrees about a vertical axis from the position shown in FIG. 4;

FIG. 6 is a bottom plan view of the bottle of FIG. 5;

FIG. 6A is a cross-sectional view of the bottle of FIG. 2, taken along the lines 6A—6A of FIG. 3;

FIG. 12 is a perspective view of an alternative embodiment of the bottle of FIG. 2, the difference being that the embodiment of FIG. 12 does not have the pronounced raised rim feature on the lower portion thereof, thereby enabling the chemical loading system to distinguish it from the bottle of FIG. 2;

FIG. 13 is a perspective view of an alternative embodiment of the bottle of FIG. 7;

FIG. 28 is an illustration of the chemical loading system of FIG. 25 when no bottles are installed; and FIG. 29 is a detailed cross-sectional view of the detection system of FIGS. 25–28.

DETAILED DESCRIPTION OF THE PREFERRED AND ALTERNATIVE EMBODIMENTS

Figure 1:
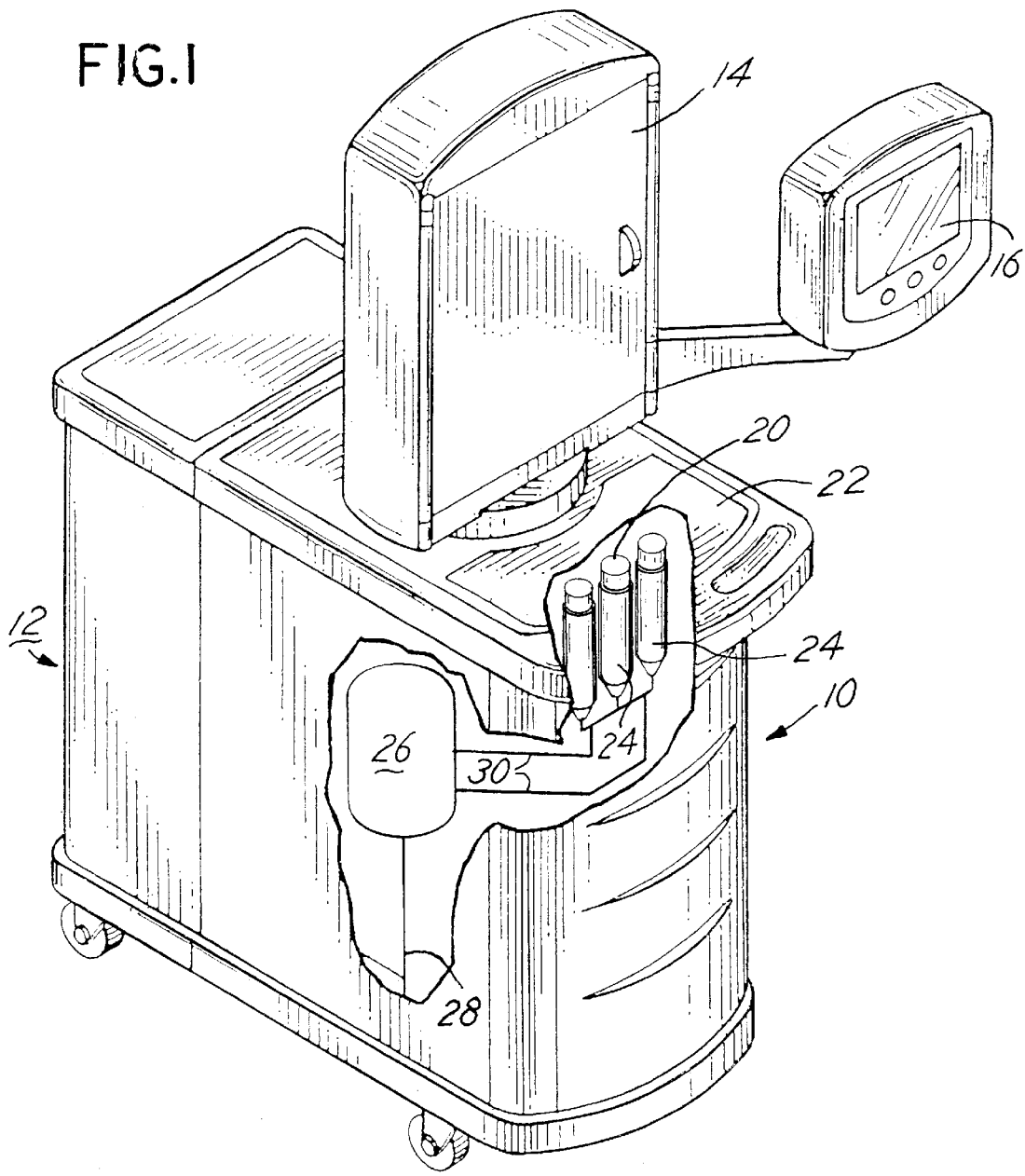
FIG. 1 is a perspective view of a dialysis machine having a batch dialysate preparation system, with the batch dialysate preparation system having a chemical loading mechanism that receives the bottles of the present invention.

Referring now to FIG. 1, a preferred embodiment of a dialysis machine 10 for use in conjunction with the inventive batch chemical vessels and chemical loading system is shown in a perspective view. In order to better appreciate the different features of the vessels and chemical loading system per se, a brief discussion of the environment in which they may be used is helpful for understanding.

The preferred dialysis machine 10 has an integral water treatment and dialysate preparation module contained within a lower cabinet 12. An extracorporeal blood circulation circuit is housed within an upper cabinet 14. The dialysis machine 10 includes a patient interface module 16 containing a touch screen display and a set of hard keys connected to two central processing units. The interface module 16, in conjunction with the central processing units, exercises supervisory control over the operation of the machine, displays the current status of the machine and treatment, and prompts the user to input commands and information.

The vessels 20 of the subject invention contain batch quantities of chemicals for preparation of physiologic, irrigation or therapeutic fluids, and are shown in FIG. 1 in an installed condition on the machine. The vessels 20 may also contain a chemical cleaning or disinfection agent such as citric acid. When the user wishes to install the vessels 20, the user removes a cover plate 22 from the top surface of the cabinet 12 and installs the vessels 20 in an upside-down orientation on a chemical loading system 24, as described in greater detail below. The chemical loading system 24 includes features to open the bottles and empty the contents of the bottle. The chemicals are conducted from the chemical loading system into a chemical mixing tank 26 sized to prepare a batch quantity of the physiologic fluid, e.g., dialysate solution. The chemicals are mixed with water supplied from the water preparation and treatment module via a connecting conduit 28.

The preferred dialysis machine 10 shown in FIG. 1 is described at length in the patent literature. The details of the dialysate preparation module, water treatment module, and extracorporeal blood circuit are not particularly important, and the interested reader is directed to U.S. Pat. No. 5,591,344 to Rodney S. Kenley et al. for further details. Therefore, a detailed discussion of these aspects of the instrument is omitted. It will be readily apparent that the bottles of the present invention could be used in other types of dialysis machines than the one shown in FIG. 1.

Referring now to FIGS. 2–6, one embodiment of a bottle 20 for containing chemicals to be introduced into a dialysis machine, such as the dialysis machine of FIG. 1, is shown in a perspective view. The bottle of FIG. 2–6 is particularly suitable for containing a unit dose of chemicals that are in a powdered form, such as a unit dose of powdered bicarbonate formulation, powdered chemical cleaning agent, powdered vitamin formulation, and so forth. The bottle 20 is adapted to be installed on the chemical loading system 24 of FIG. 1 in order to open the bottle and introduce the chemicals into a fluid path in the dialysis machine, such as for example fluid conduits 30 connecting the chemical loading system 24 to the batch dialysate preparation tank 26.

The bottle 20 of FIG. 2 consists of a bottle shell 32 having a sidewall 34 defining a bottle axis 36, an upper shoulder portion 38, a comer portion 40 at which the shoulder portion 38 intersects the sidewall 34, a lower portion 42, and a mouth 44 through which the chemicals may be withdrawn from the bottle when it is either filled or when the contents are dispersed during use. Preferably, the bottle is made by a blow-molding process.

The mouth 44 of the bottle is sealed with a membrane after filling, but the membrane is not shown in FIG. 2 in order to better illustrate the other features of the bottle. Preferably, the sealing membrane is a very low oxygen and water permeability film. The membrane is illustrated in the cross-section of FIG. 6A as reference numeral 49.

Figure 23:
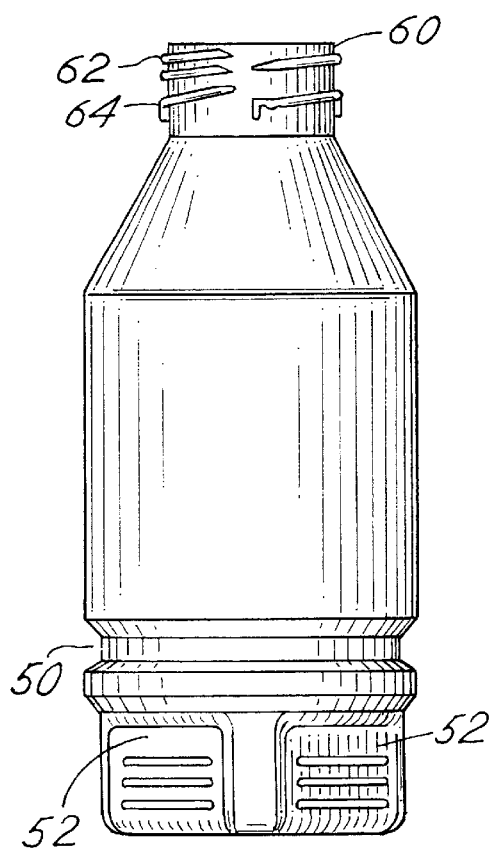
FIG. 23 is an elevational view of a bottle of the type shown in FIG. 2, in which the detection feature takes the form of a circumferential-disposed groove or indented rim on the sidewall of the bottle positioned a predetermined distance away from the mouth of the bottle.
Figure 24:
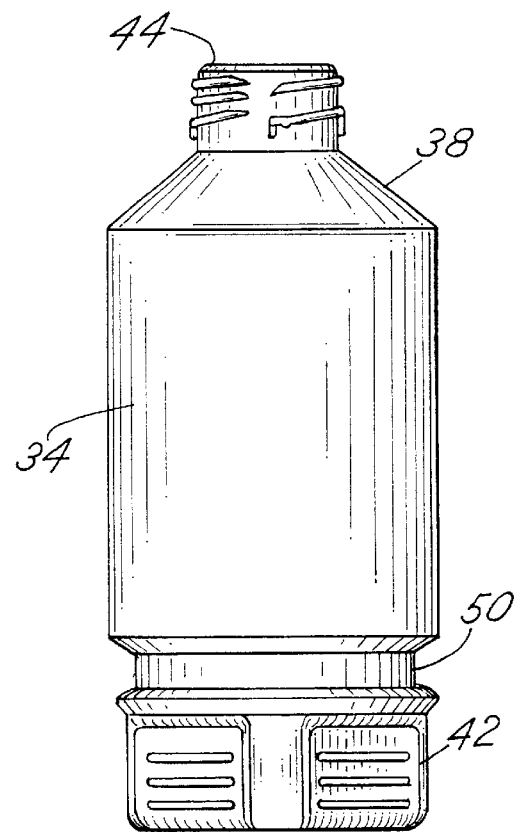
FIG. 24 is an elevational view of a bottle of the type shown in FIG. 7, in which the detection feature takes the form of a circumferential-disposed groove or indented rim on the sidewall of the bottle positioned a predetermined distance away from the mouth of the bottle.

The bottle further includes a detection feature comprising a physical configuration on the exterior of the bottle shell at a predetermined location or distance from the mouth of the bottle, where it will be detected by a detection system located inside the dialysis machine when the bottle is installed on the chemical loading system. In the illustrated embodiment of FIG. 2, the detection feature takes the form of a raised rim 50 extending outwardly from the bottle sidewall 34. In the embodiment of FIGS. 23 and 24, the detection feature 50 takes the form of a circumferential groove or indented rim in the sidewall of the bottle shell.

Referring to FIG. 2 again, the rim extends around the circumference of the sidewall in a manner perpendicular to the bottle axis 36. The raised rim 50 is positioned on the sidewall 34 a predetermined distance away from the corner portion 40 and the bottle mouth 44. As will be more fully understood later in the discussion of FIG. 14, the distance separating the rim 50 from the corner portion 40 and the mouth is dictated by the design of the holding structure in the chemical loading apparatus. It is also dictated by the design of a mechanical, or optionally, an optical detection system in the chemical loading system, in that the detection feature must be placed at the location where the detection system is in the machine when the bottle is installed on the chemical loading system. The detection system detects the presence of the bottle in the chemical loading system and thereby discriminates between a bottle having the rim 50 from a bottle that does not have the rim, such as the bottle shown in FIG. 12 or FIG. 23. The configuration of the bottle of FIG. 2 is such that when the bottle is installed on the chemical loading system 24 of FIG. 1, the rim 50 engages a detection system in the chemical loading system, enabling the presence of the bottle to be detected and the bottle discriminated from a bottle without the raised rim. To insure reliable detection of the rim 50, the rim has a height (measured in a direction perpendicular to the bottle axis 36) of at least 0.1 or 0.2 inches, and a length L (measured along the bottle axis) of between 0.25 and 0.5 inches in the illustrated embodiment.

The shape of the shoulder portion 38 of the bottle is designed to promote the ready emptying of a powdered chemical formulation from the bottle, such as a sodium bicarbonate formulation. In particular, as shown in FIG. 5, the shoulder portion 38 comprises a frusto-conical wall having a cone angle $\alpha$ of between about 60 and about 70 degrees, and a height H of between one-half and two inches. Additionally the interior bottle surface may be treated for low friction and smooth flow characteristics to promote release of the contents of the bottle. Fluorination of the bottle surface is one possible method.

The width W of the mouth 44 of the bottle of FIGS. 2–6 is also widened sufficiently to allow quick emptying of the bottle contents. In the illustrated embodiment, the mouth 44 has a diameter of between 1 and 2 inches. The ratio of the width of the mouth to the diameter of the bottle is about 1:2, and the ratio of the width of the mouth to the height of the bottle is between 1:4 and 1:5 in the illustrated embodiment.

Referring to FIGS. 2, 4, 5 and 6, the lower portion 42 of the bottle further comprises a plurality of flat sides 52 oriented parallel to the bottle axis 36 and arranged around the bottom of the bottle and intersecting one another, as best shown in FIG. 6. The sides 52 have small raised gripping ribs 54 forming a knurled surface on the sides 52. The ribs 54 and configuration of the sides 52 promote the gripping of the bottle. The bottom surface 56 of the bottle has a slightly domed shape as best shown in the cross-section of FIG. 6A at 59, and a transverse reinforcing rib 58.

Referring now to FIGS. 2–5 and 6A, the bottle 20 further comprises a top portion 60 having a first set of split screw threads 62 for receiving a protective cap for the bottle (not shown), which protects the membrane sealing the mouth 44. The split screw threads 62 are positioned adjacent to the bottle mouth 44, as shown. A second set of screw threads 64 are also formed on the top portion 60. The screw threads 64 are used for mounting the bottle 20 to a bottle opening apparatus in the chemical loading system. The screw threads 64, which may take the form of bayonet screw threads, are positioned below the split screw threads 62. FIGS. 4 and 5 show the bottle rotated between a 90 degree angle, to better illustrate the screw thread features 62 and 64 of the illustrated embodiment. The bayonet screw threads give the user a positive feeling when the bottle is twisted onto the bottle mounting structure in the chemical loading system, described in detail below.

Figure 7:
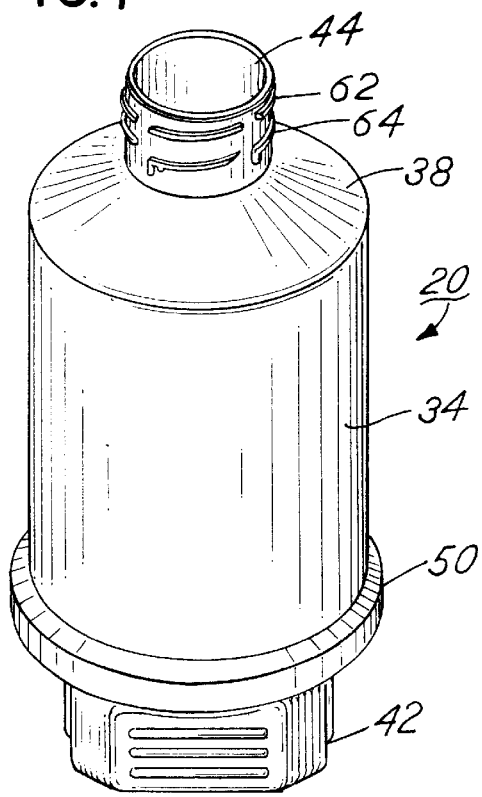
FIG. 7 is a perspective view of an alternative embodiment of the bottle of FIG. 2.
Figure 8:
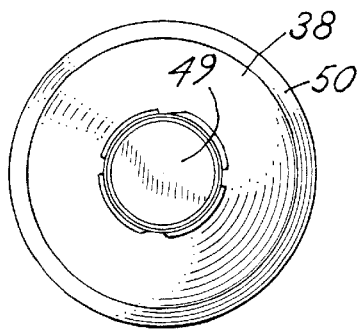
FIG. 8 is a top plan view of the bottle of FIG. 7.
Figure 9:
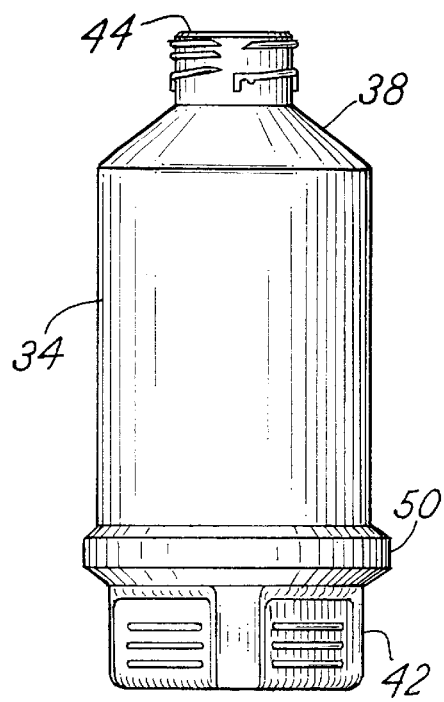
FIG. 9 is a side elevational view of the bottle of FIG. 7.

FIGS. 7–11 illustrate an alternative embodiment of the bottle of FIG. 2. The structural components of the bottle of FIGS. 7–11 are the same as for the bottle of FIGS. 2–6A, hence like reference numbers refer to like elements in the various views. The bottle of FIG. 7 is particularly suitable for containing a liquid chemical formulation, such as a liquid acid dialysate chemical formulation or a liquid chemical cleaning or disinfection agent.

Figure 20:
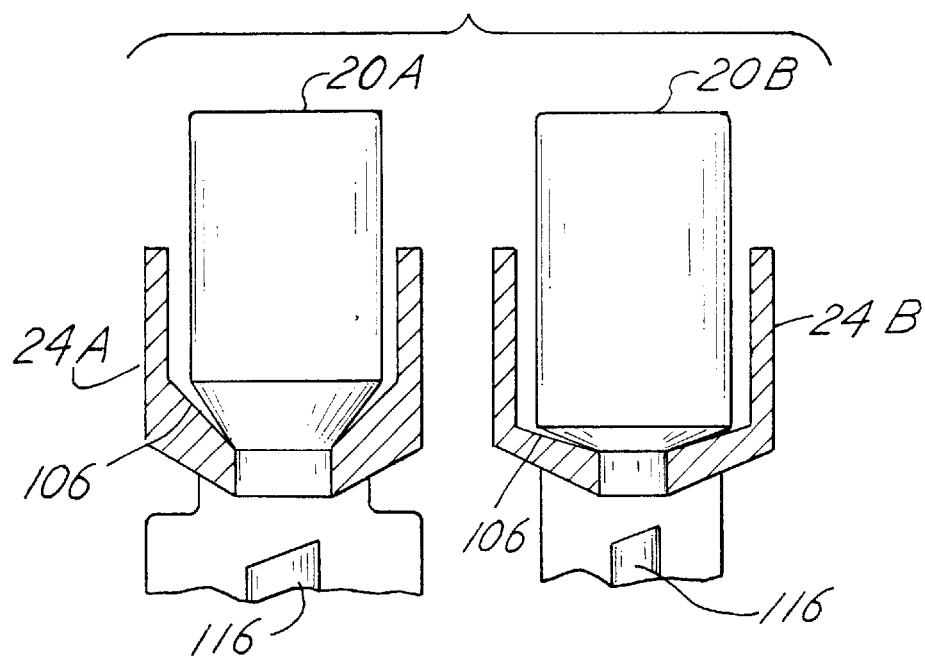
FIG. 20 is a simplified illustration of the bicarbonate formulation and liquid acid formulation bottles of FIGS. 2 and 7 shown side by side installed in their respective bottle mounting structures, as they would be when they are correctly installed on their respective mounting systems, and showing how the bottle mouth width and the shape of the shoulder portion of the bottles cooperate with features in the opening mechanism to insure that the bottles are correctly installed on the proper bottle opening and mounting units.
Figure 21:
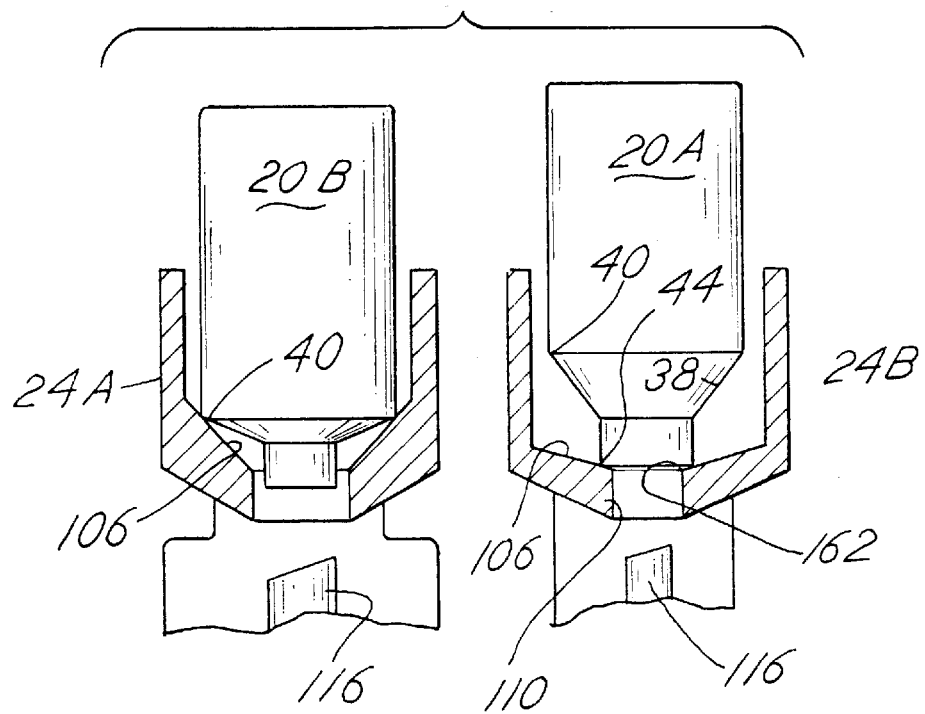
FIG. 21 shows what happens when a user attempts to install the bottles of FIGS. 2 and 7 on the wrong bottle opening mechanisms, with the differences in the width of the mouth of the bottle, and the different shape of the shoulder portions of the bottles, preventing the bottles from being fully engaged to the bottle mounting and opening mechanisms.

The primary differences between the bottle of FIGS. 7–11 and the bottle of FIGS. 2–6A are that the bottle of FIGS. 7–11 is given a different height and configuration for the shoulder portion, a different cone angle $\alpha$, and different width W of the mouth 44. These differences in the configuration of the bottle of FIGS. 7–11 enable two different chemical loading system configurations to be made for the dialysis machine, each designed to receive one of the type types of bottles but not the other. The chemical loading system that is designed to accommodate a bottle having the configuration of FIGS. 2–6A (a type "B" bottle, where B stands for bicarbonate) will not accept a bottle having the configuration of FIGS. 7–11 (a type "A" bottle, where A stands for acid), and a chemical loading system designed to accommodate a bottle having the configuration of FIGS. 7–11 will not accept a bottle having the configuration of FIGS. 2–6. This prevents the user for accidentally installing two liquid acid bottles or two powdered bicarbonate formulation bottles in the dialysis machine. This aspect of the invention is illustrated in FIGS. 20 and 21 and will be described in further detail below.

Figure 10:
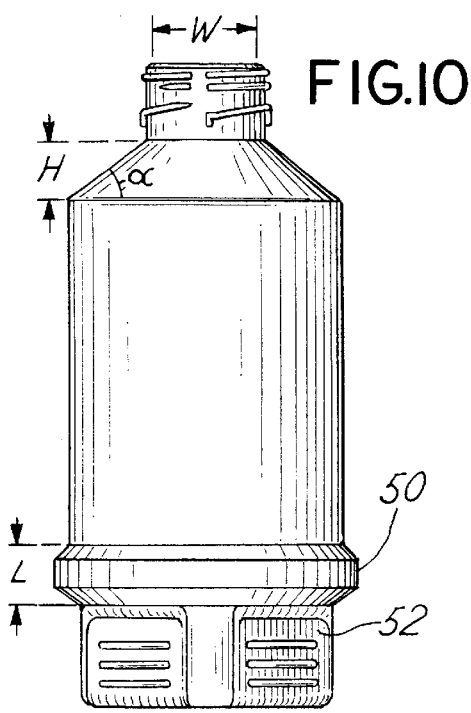
FIG. 10 is another side elevational view of the bottle of FIG. 7, with the bottle shown rotated 90 degrees about a vertical axis from the position shown in FIG. 9.
Figure 11:
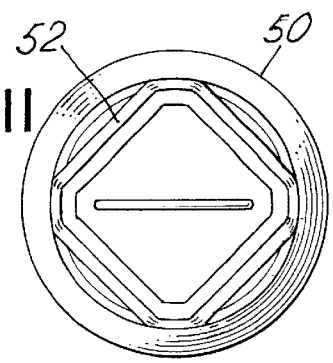
FIG. 11 is a bottom plan view of the bottle of FIG. 7.

Referring to FIG. 7 and 10, since this embodiment of the bottle is designed to contain chemicals in a liquid phase, and such liquids will more readily fall from the bottle into the chemical loading system, the mouth 44 of the bottle of is given a narrower width W as compared to the bottle of FIG. 2. Additionally, the height H of the shoulder 38 is substantially less. The cone angle α, (FIG. 10) is between 30 and 40 degrees in the illustrated embodiment, such as 38 degrees. Note that the bottle of FIGS. 7–11 includes a detection feature in the form of a raised rim 50.

FIG. 12 shows another embodiment of the inventive bottle. The bottle of FIG. 12 is identical to the bottle of FIG. 2, with the sole exception that the bottle does not have the prominent raised rim feature 50 of FIG. 2. The bottle of FIG. 12 would for instance contain a batch quantity, powdered, chemical cleaning formulation. The absence of the rim enables the detection system in the chemical loading system to discriminate between a loaded bottle that contains powdered dialysate chemical formulations (the bottle of FIG. 2) from a bottle containing a powdered chemical formulation (the bottle of FIG. 12). Of course, the software for the machine and could be changed to associate a bottle without a rim 50 as the bottle containing the powdered bicarbonate formulation and the bottle with the rim to contain the chemical cleaning agent, if that is how the bottles are in fact loaded. Either way, the presence or absence of the detection feature, along with the detection system in the machine, will prevent the wrong type of chemicals from being accidentally introduced into the machine, promoting patient safety. The small raised ring feature 70 in FIG. 12 is merely to assist in the placement of a label on the side wall 34 of the bottle, and would not trigger a detection of a rim feature such as the rim 50 of FIG. 2. The small raised ring 70 could be eliminated if there is any risk of the ring 70 being detected as a raised rim 50.

FIG. 13 shows another alternative embodiment of the bottle. The embodiment of FIG. 13 is identical to the embodiment of FIG. 7, except that it does not have the pronounced raised rim feature 50. The small ring 70 assisting placement of a label on the side wall 34 could be eliminated if desired.

Figure 14:
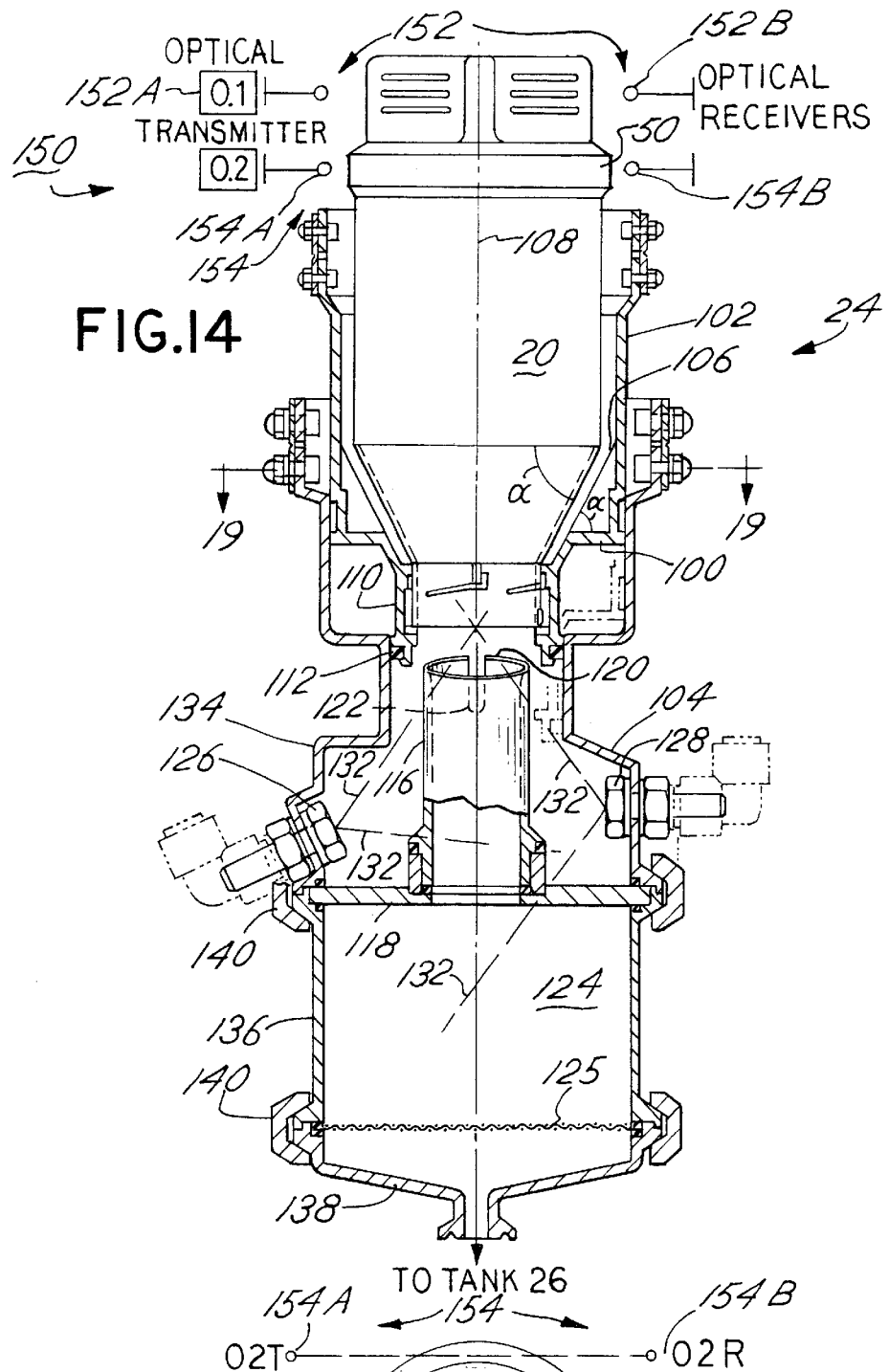
FIG. 14 is an illustration of the bottle of FIG. 2 installed on a bottle mounting structure in the dialysis machine of FIG. 1, showing how the rim feature on the lower portion of the bottle shell sidewall interacts with an optical sensor assembly in the bottle opening mechanism to detect the presence of the bottle and the type of the bottle.

FIG. 14 is an illustration of the bottle of FIG. 2 installed on a bottle mounting structure 100 and chemical loading system 24 in the dialysis machine of FIG. 1. FIG. 14, together with FIG. 14A, also shows how the rim feature 50 on the lower portion of the bottle interacts with an optical detector assembly in the chemical loading system 24 to detect both the presence of the bottle and the type of the bottle (i.e., a bottle with a raised rim 50).

Referring primarily to FIG. 14, the chemical loading system includes a bottle mounting structure 100 consisting of an upper, cylindrically-shaped bottle receiving case 102, and a lower, cylindrically-shaped outside bottle receiving case 104. The upper case 102 includes a set of angled ribs 106 oriented at an angle relative to the chemical loading system axis 108. The angle of inclination is substantially the same as the cone angle α of the bottle 20. The angled ribs 106 are also given a height substantially the same as the height H of the shoulder portion 38 of the bottle 20 (FIG. 5) so that the bottle of FIG. 2 can nest snugly within the upper case 102, as shown in FIG. 14. The angled ribs 106 could also take the form of a inverted section of a right circular cone to get the desired holding action to mate with the exterior configuration of the shoulder of the bottles. (see FIGS. 21 and 22) The chemical loading system 24 also includes a mounting structure 110 that receives the mouth of the bottle 20 and engages the bayonet screw threads on the top of the bottle when the bottle is twisted onto the mounting structure 110. The diameter of the mounting structure 110 is designed to accommodate a bottle having the same mouth width W of FIG. 5.

The entire upper case 102 moves up and down relative to the lower case 104 by means of an agitation motor assembly that is mechanically fastened to the upper case 102. The agitation motor assembly 200 is shown in FIGS. 14B and 17–19 and is described subsequently. The purpose of the agitation motor assembly 200 is also to impart a low frequency, small amplitude vibratory motion to help promote the release of the entire contents of the bottle. A primary O-ring seal is provided at 112 to seal the upper case 102 and prevent any fluids from escaping around the periphery of the mounting structure 110 and into the space between the upper case 102 and the lower case 104.

The chemical loading system 24 also includes a knife or bottle piercing member 116 mounted to a stay 118 extending across the upper region of the lower case 104. The knife remains fixed in position. The upper edge 120 of the knife 116 pierces the membrane seal at the top of the bottle when the agitation motor assembly moves the bottle from the upper position shown in FIG. 14 to a lower position. In the lower position, the upper edge of the knife 116 cuts a circular hole in the membrane, with the portion 122 of the knife leaving a small attachment or connecting piece connecting the periphery of the membrane and the central part of the membrane to keep the cut portion of the membrane from being disconnected from the rest of the bottle. This technique is described in further detail in U.S. Pat. 5,788,099 to Dennis M. Treu, et al., the contents of which are incorporated by reference herein.

When the bottle is moved to the lower position and the membrane pierced by the knife 116, the contents of the bottle fall into an upper dissolving vessel or tank 124 defined by the side walls of the lower case 104. A stainless steel screen 125 (50–100 micron size) is placed in the bottom of the tank 124. Three spray nozzles are provided in the upper dissolving tank 124 to promote the dissolution of the powdered chemical composition. Two of the spray nozzles 126 and 128 are shown in FIG. 14. A third spray nozzle 130 is shown in FIG. 14B, which is another elevational view of the chemical loading system shown in FIG. 14, but rotated 90 degrees relative to the view shown in FIG. 14. The spray nozzles 126, 128 and 130 are connected to a source of water in the dialysis machine and direct a stream of water in the direction bounded by the lines 132. The stream of water from the jets 126, 128 and 130 promotes rapid dissolution of any clumps of powdered chemicals that may accumulate on the screen 125, thereby shortening the time required to prepare a batch of the solution in the main chemical mixing and storage tank 26 of FIG. 1.

The lower case 104 is shown as comprising upper, middle and lower members 134, 136 and 138, respectively, which are retained together in a secure, water-tight condition by means of clamps 140. This construction eases manufacturing and installation of the screen 125.

Figure 14A:
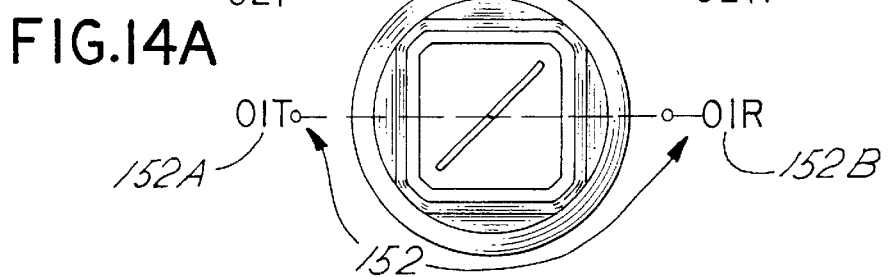
FIG. 14A is a schematic plan view of the bottom of the bottle of FIG. 14, showing the position of the optical transmitters and receivers relative to the bottle.
Figure 14B:
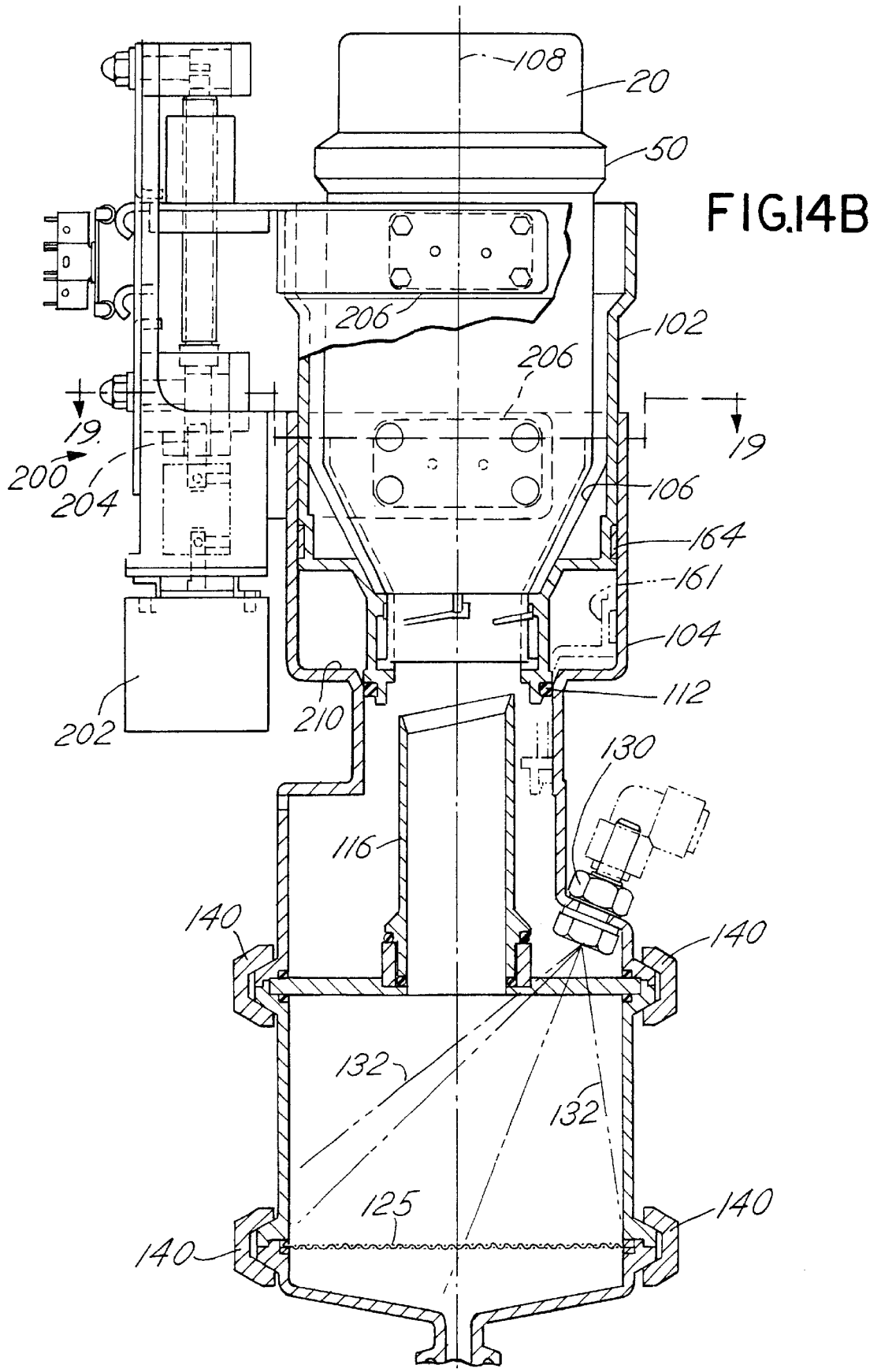
FIG. 14B is a detailed cross-sectional views of the chemical loading system of FIG. 14, shown rotated 90 degrees in order to illustrate an agitation motor assembly and third spray nozzle.

Referring now to the top of FIG. 14 and to FIG. 14A, the illustrated embodiment includes an optical detection system 150 for detecting when a bottle has been loaded into the chemical loading system 24, and for detecting whether the bottle that has been installed has a raised rim 50 or not. An alternative mechanical detection system using a lever or probe that is moved by the detection feature 50 to operate a switch or sensor is described below in conjunction with FIGS. 25–29.

The optical detection system 150 includes two optical transmitters and two receivers. One set 152 of transmitters and receivers detects the presence of the bottle. The optical transmitter 152A and receiver 152B are positioned on opposite sides of the chemical loading system, as indicated in FIGS. 14 and 14A. The presence of the bottle installed in the chemical loading system 24 interrupts the signal from the optical transmitter 152A, and the optical receiver 152B sends a signal indicting that a bottle is present to the control system for the dialysis machine.

The second set 154 of transmitters and receivers is placed at the same elevation as the rim feature 50, and oriented tangential to the side wall 34 of the bottle shell. If the protruding raised rim feature 50 is present, it will be in the optical path between the transmitter 154A and receiver 154B, as shown in FIG. 14A. This interruption of the signal is sent to the control system. Similarly, if no rim 50 is present on the side of the bottle, but the first set 152 indicates that a bottle is installed, then the control system knows that the bottle that is installed is a type that has no raised rim. If that type of bottle contains cleaning agents instead of powdered bicarbonate formulation, the user can be prompted to replace the bottle with the correct bottle. Note also that this prompting of the user will take place before the bottle is opened. The chemical loading system will only open the bottle when the software for the machine indicates that the two pairs of detectors are sending signals that both a bottle is installed, and the bottle is the correct bottle for that chemical loading system (i.e., rim or no rim).

Figure 15:
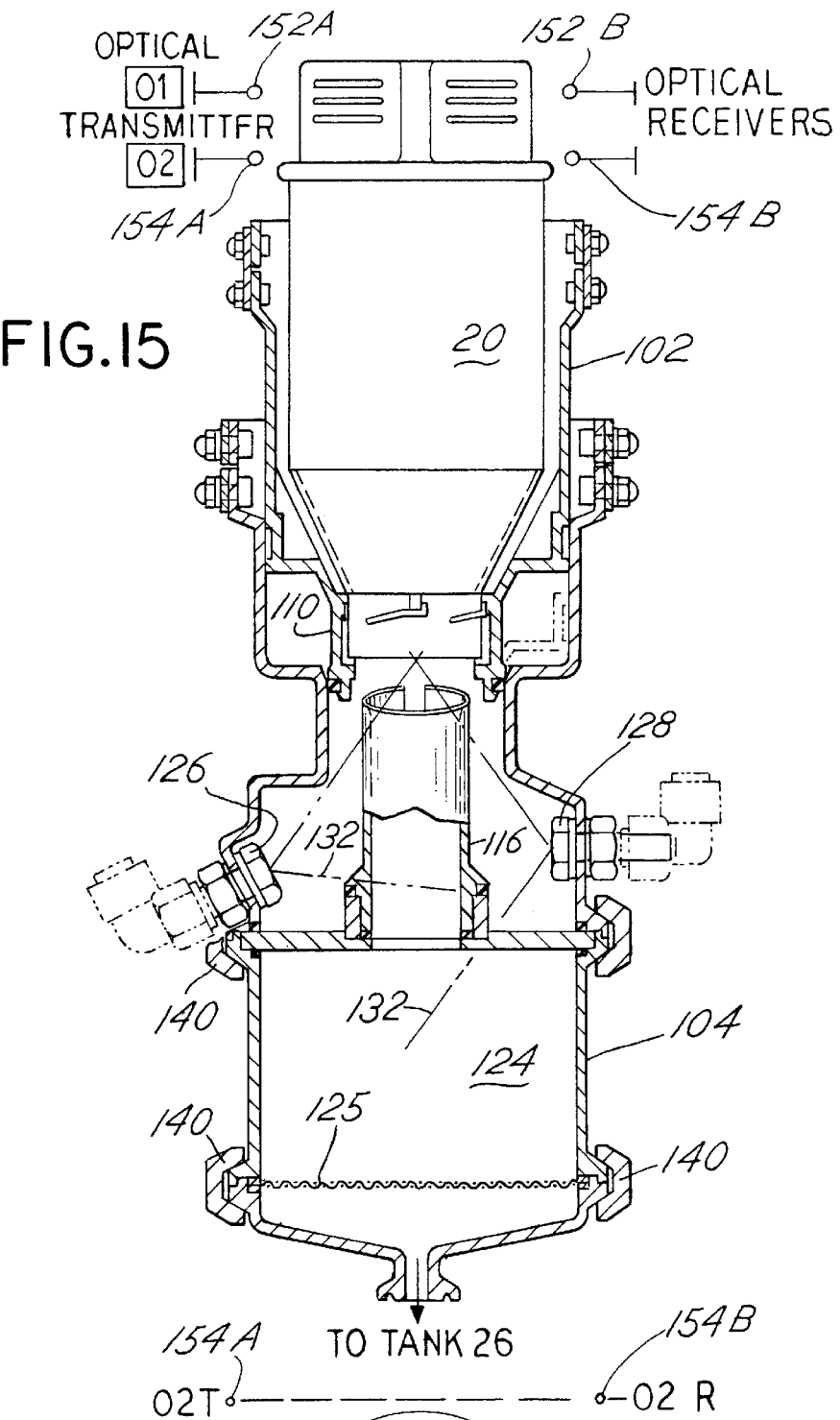
FIGS. 15 and 15A illustrate the bottle of FIG. 12 installed on a bottle mounting structure of a dialysate preparation system for a dialysis machine similar to FIGS. 14 and 14A, showing how the absence of the rim feature on the lower portion of the bottle shell sidewall interacts with the optical sensor assembly in the bottle opening mechanism to differentiate the bottle of FIG. 12 from the bottle of FIG. 2.
Figure 15A:
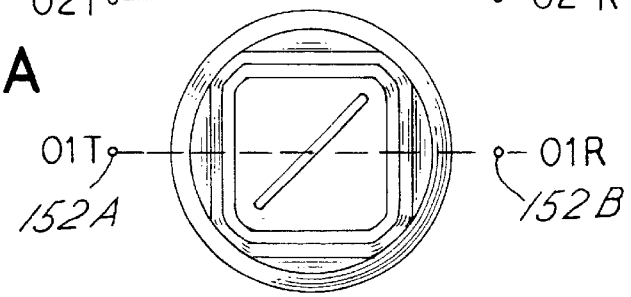

FIG. 15 shows the chemical loading assembly of FIG. 14, but with a bottle of the type shown in FIG. 12 installed. Note that the bottle 20 of FIG. 15 does not have the pronounced raised rim feature 50. Thus, as shown in FIG. 15A, the optical receiver 152B will detect the bottle in the chemical loading system 24, but the optical receiver 154 does not detect the presence of a raised rim. Therefore, in the present example the software for the dialysis machine will determine that the user has installed a chemical cleaning bottle (without a rim 50) instead of a bicarbonate formulation bottle (with a rim 50) on the chemical loading system.

Figure 16:
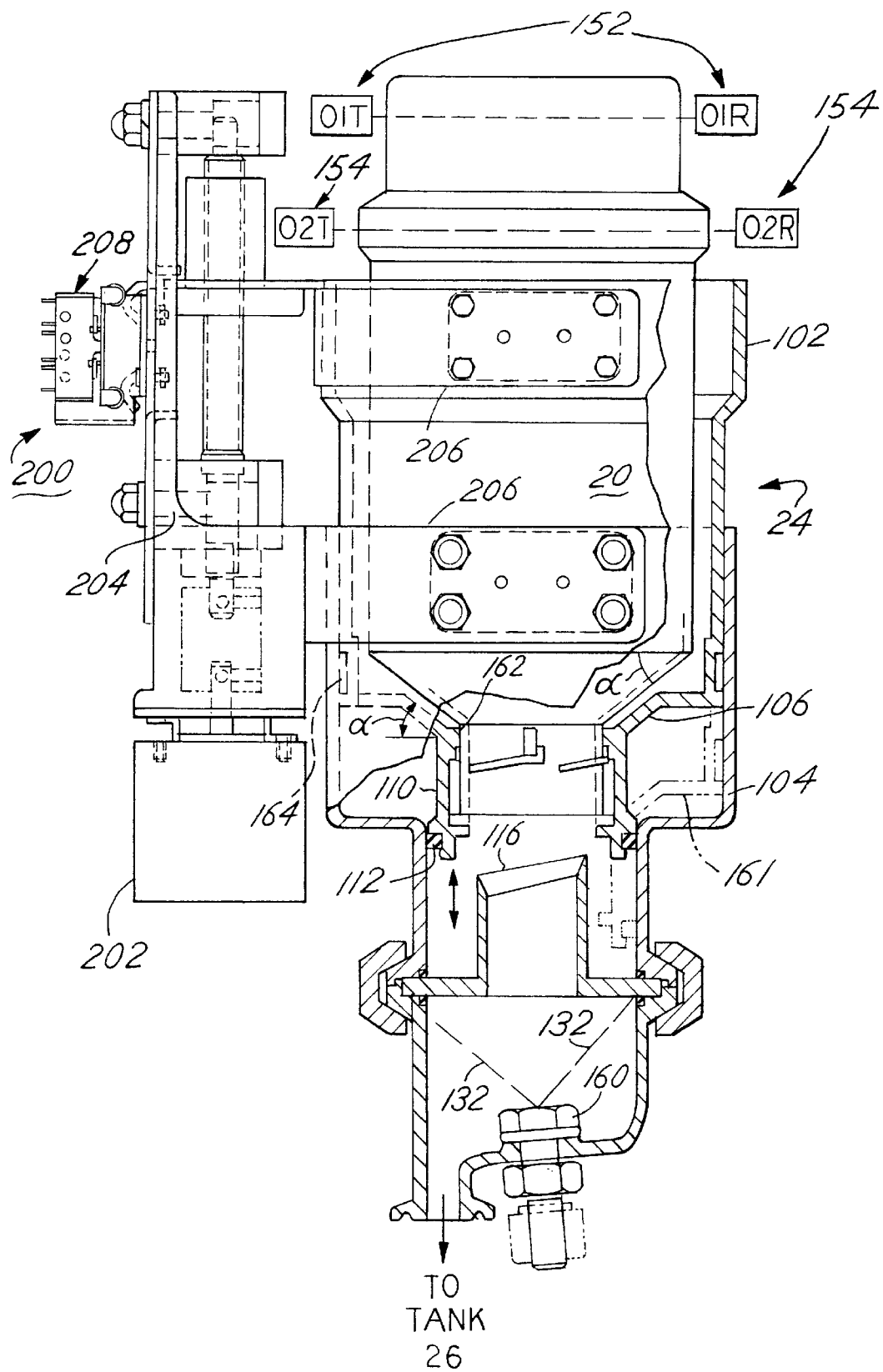
FIG. 16 is an illustration of the bottle of FIG. 7, mounted to its respective bottle opening mechanism.

FIG. 16 is an illustration of the bottle of FIG. 7, mounted to its respective bottle opening mechanism in a chemical loading system designed or adapted to receive bottles having the structure of FIG. 7, such as bottles containing liquid acid formulations or liquid cleaning or disinfection chemicals. The chemical loading system 24 includes the upper case 102, a lower case 104, a bottle mounting structure 110 integral with the upper case 102, a knife 116, and a spray nozzle 160. The spray nozzle 160 can be used for either rinsing the interior of the bottle or directed heated water to the surface of the membrane covering the mouth of the bottle during a disinfection process, as taught in Kenley et al., U.S. Pat. No. 5,591,344.

The rib 106 of the upper case 102 is given a much shorter height and a different inclination angle to match the cone angle a of the bottle 20. Furthermore, the entrance aperture 162 of the mounting structure 102 is sized to accommodate the narrower mouth of the bottle of FIG. 7. These combination of features are designed to insure that only the bottle having the configuration of FIGS. 7 and 13 can be installed in the chemical loading apparatus 24 of FIG. 16.

Note also that the system of FIG. 16 also includes two sets of optical detectors and receivers 152 and 154. They function to detect the bottle and the rim 50 of the bottle in the same manner as described in conjunction with FIGS. 14 and 14A.

Figure 17:
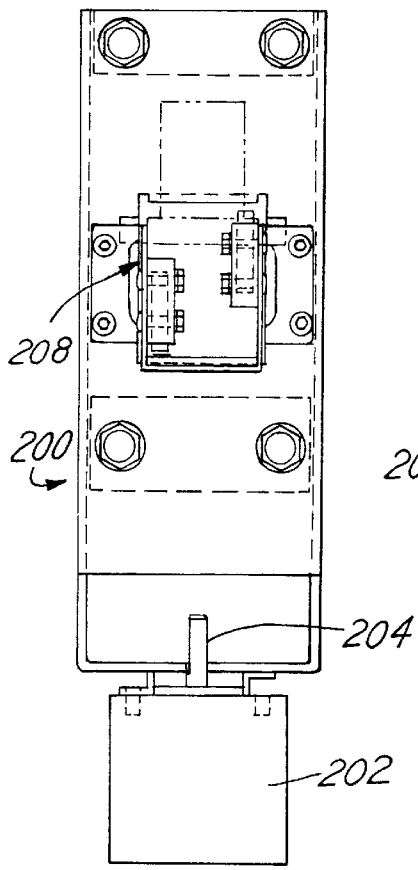
FIG. 17 is an elevational view of the motor assembly of FIG. 14B.
Figure 18:
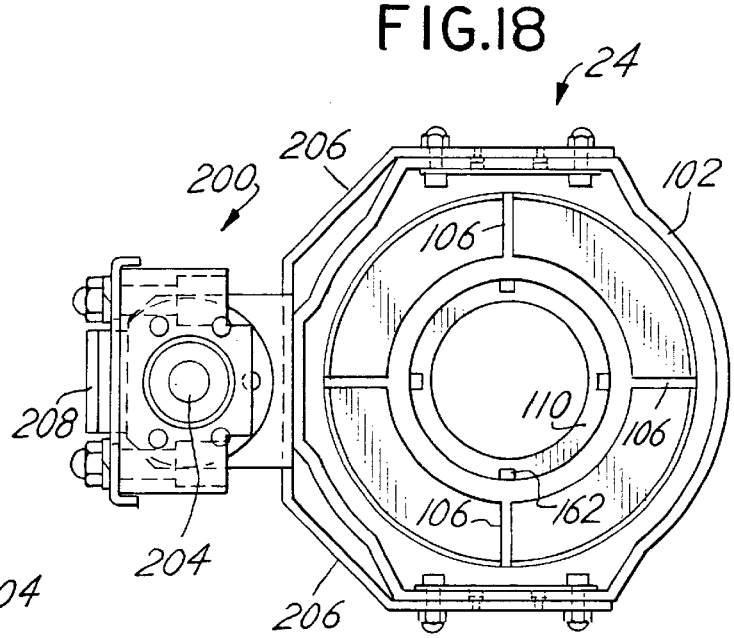
FIG. 18 is a top plan view of the chemical loading structure of FIG. 14, with the bottle omitted in order to better illustrate the chemical loading system.
Figure 19:
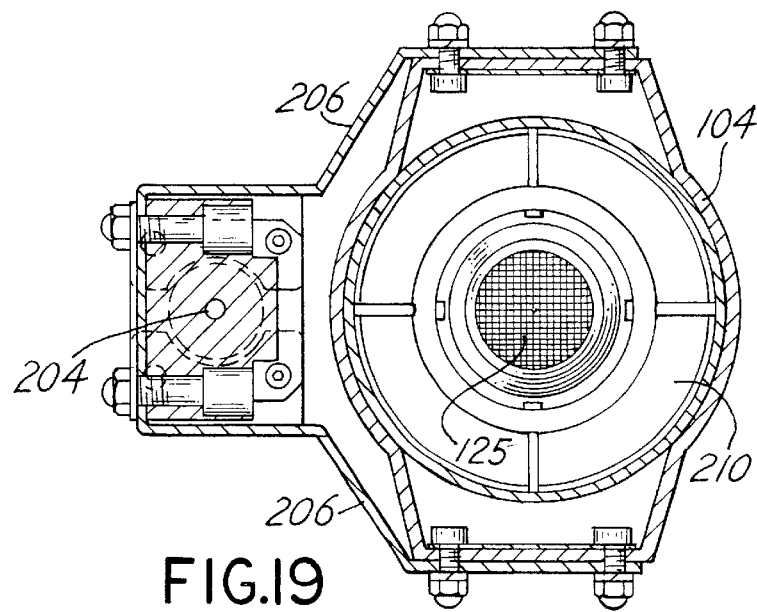
FIG. 19 is a cross-sectional view of the chemical loading system of FIG. 14, taken along the lines 19—19 of FIGS. 14 and 14B.

The chemical loading systems of FIGS. 14, 14B and 16 include a motor assembly depicted generally as reference numeral 200, shown best in FIGS. 14B, 16 and in FIGS. 17–19. The motor assembly 200 is designed to move the upper case 102 and bottle mounted therein up and down along the central axis of the chemical loading system in order to open the vessel. In particular, the upper case 102 is moved from an upper position shown in FIGS. 14 and 16 to a lower position (indicated in dashed lines at 161), in which the knife 116 cuts through the membrane covering the mouth of the bottle. The contents of the bottle fall into the mixing chamber 124, where they are conducted from the bottom of the chamber 124 to intermediate fluid conduits and into the tank 26 of FIG. 1. After emptying the contents of the bottle 20, the motor assembly 200 moves the bottles to the upper position. A secondary sliding seal 164 is positioned on the lower portion of the upper case 102 to assist in preventing any fluid from migrating out of the chemical loading system 24.

The motor assembly 200 includes a stepping motor 202, a lead screw drive mechanism 204, and a pair of brackets 206 that fasten to the upper case 102 of the chemical loading system and to the moving part of the lead screw drive mechanism 204. FIG. 17 shows the motor assembly in a side elevational view. It will be appreciated that the motor assembly includes suitable mounting brackets that connect the motor assembly 200 to the dialysis machine, such that the motor 202 can move the bottle 20 and upper case 202 relative to the fixed part of the system, namely lower case 104 and components placed therein. The motor assembly includes an upper and lower limit sensor and switch assembly 208 to control the raising and lowering of the agitation motor assembly. These details, and further details on the motor assembly, are not particularly important to the present invention and can be modified from the illustrated embodiment.

FIG. 18 is a top plan view of the assembly of FIG. 14, with the bottle and knife removed in order to better illustrate the structure of the chemnical loading system. FIG. 19 is a cross-sectional view of the assembly of FIG. 14B taken along the lines 19—19, but with the upper case and knife assembly removed in order to better illustrate the structure of the lower holder or case 104 and peripheral shoulder surface 210 of FIG. 14B.

Further details on the design of the holders of FIG. 14 are not particularly relevant. The invention is applicable to other chemical loading structures, such as the chemical loading structures shown in the Kenley et al. '344 patent, or an entirely different chemical loading system that may be worked out by persons skilled in the art from the present disclosure.

FIGS. 20 and 21 illustrate, in a somewhat simplified form, how the chemical loading systems of FIGS. 14 and 16 cooperate with the shape of the bottles of FIGS. 2 and 7 to only allow the proper bottle to be installed in the chemical loading system. In FIG. 20, chemical loading system 24A is of the configuration shown in FIG. 14, and receives a bottle of the shape shown in FIG. 2, indicated as bottle 20A. Chemical loading system 24B is of the configuration of FIG. 16, and receives a bottle of the shape shown in FIG. 7, indicated as bottle 20B. The wall 106 is shown as having a slightly different inclination from the cone angle of the bottle, indicating that the wall 106 does not have to exactly match the cone angle and height of the shoulder portion of the bottle for the system to work as designed.

As indicated in FIG. 21, if user attempts to install the bottle 20B on the chemical loading system 24A, an interference occurs where the corner 40 of the bottle intersects the wall 106. The bottle cannot be lowered in the chemical loading system for the bayonet screw threads to engage the bottle mounting member 110 in the chemical loading system. This is of course apparent to the user, and so they realize that they are installing the wrong type of bottle on the chemical loading mechanism 20A. If the user attempts to install the bottle 20A onto the chemical loading system 24B, the wide mouth 44 of the bottle 20A will not fit in the entrance aperture 162 of the bottle mounting structure 110. Note also the pronounced mismatch between the shoulder 38 of the bottle 20B and the gently sloping wall 106, indicating a substantial amount of play or movement is available. Again, due to the mouth of the bottle being too wide for the entrance aperture 162, the bayonet screw threads will not engage the bottle mounting structure 110. The interference or misfit shown in the right hand side of FIG. 18 is readily apparent to the user, indicating to them to remove the bottle 20A and instead insert a bottle of the correct configuration, i.e., the bottle 20B. Thus, as will be appreciated from the above discussion and FIGS. 2, 7, 14 and 16, the chemical loading system and bottle configurations enable precise control over the installation of the bottles in the machine and minimize the possibility of human error in how the bottles are loaded into the machine.

Figure 22:
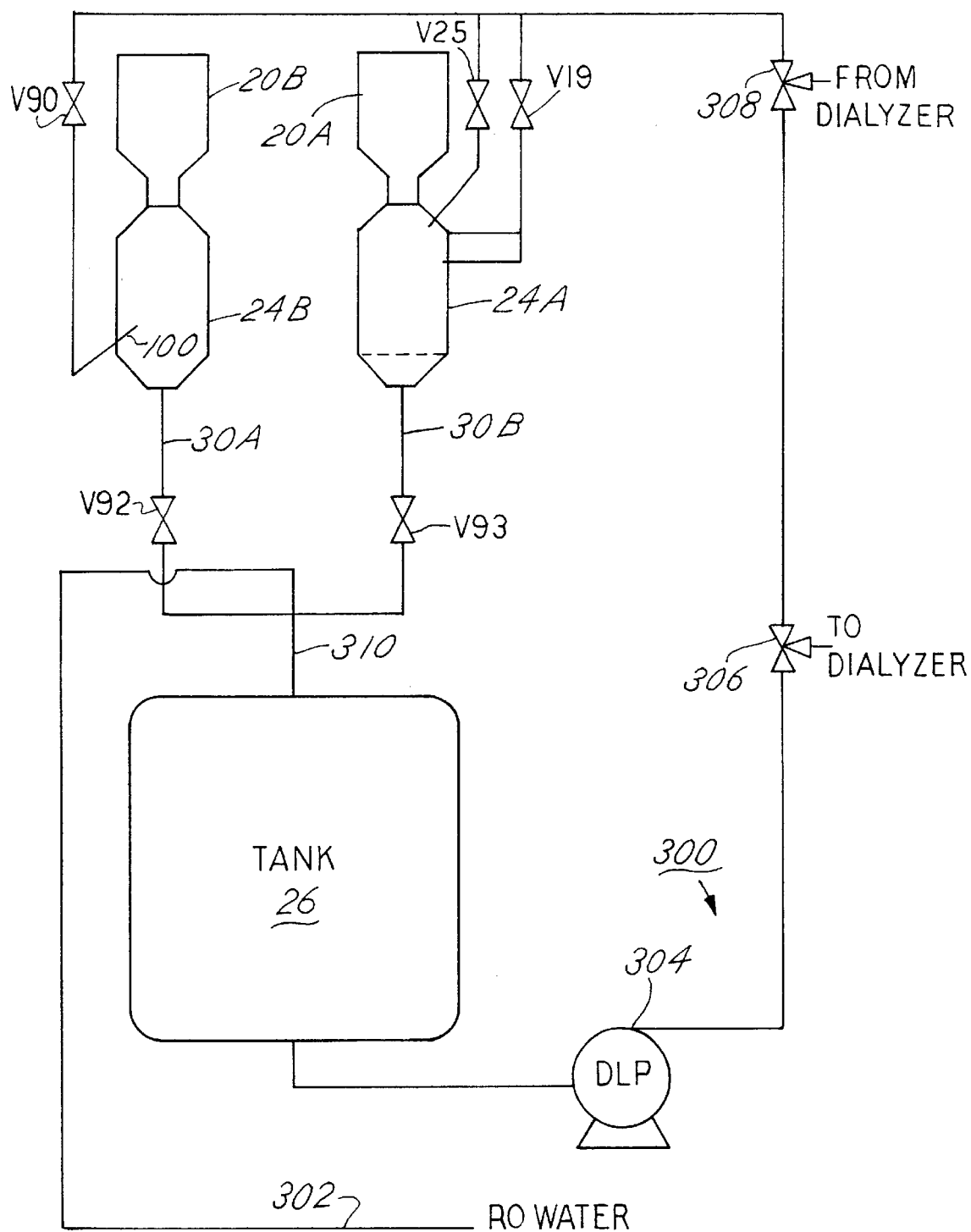
FIG. 22 is a schematic diagram showing the flow path for preparation of a dialysate solution in the dialysis machine of FIG. 1 for the bottles of FIGS. 2 and 7.

FIG. 22 is a schematic diagram showing the flow path for preparation of a dialysate solution in the dialysis machine of FIG. 1. The dialysis machine includes a water preparation and treatment module that supplies reverse osmosis filtered water to the tank 26 via a conduit 302. The outlet of the tank 26 is connected to a dialysate circulation loop 300 comprising, among other things, a dialysate pump 304, a three-way valve 306 (with one branch leading to the inlet of dialyzer filter, not shown), a three-way valve 308 (with one branch connected to the outlet of the dialyzer filter), and a set of valves V90, V25 and V19. Valve V90 is connected to the spray nozzle 160 of FIG. 16. The outlet of the chemical loading system 24B is connected to a line 30A, which has a valve V92 controlling the flow of fluid through the line and into the tank 26.

Valves V25 and V19 control the flow of fluid to the three spray nozzles provided for the powdered chemical loading system 24A. The outlet of the powdered chemical loading system 24A is connected to a line 30B, which has a valve V93 controlling the flow of fluid through the line and into the tank 26. The water and chemicals from the chemical loading systems all flow into the tank 26 via an inlet line 310 at the top of the tank.

Further details on the dialysate preparation system are disclosed in U.S. Pat. No. 5,591,344, therefore a detailed discussion is omitted here for the sake of brevity.

FIG. 23 shows an alternative embodiment of the powdered formulation or "B" bottle, in which the detection feature takes the form of a groove or indented ring 50 extending around the periphery of the sidewall of the bottle. FIG. 24 shows an alternative embodiment of the liquid or "A" bottle, which has a detection feature in the form of a groove 50. When the bottle of this embodiment is installed on the bottle opening apparatus, the presence of the indented ring or groove is detected by the detection system using either optical or mechanical means. For example, if the optical system is used, one set of optical emitter and detectors are placed tangential to the side of the bottle and in alignment with the groove. A second set of emitter and detectors is placed immediately above and below the first set. The optical path between the emitter and detector in the second set is interrupted by the sidewall of the bottle, indicating the presence of a bottle in the bottle mounting apparatus. The optical path between the emitter and detector in the first set is not interrupted, due to the presence of the groove or depression in the side wall of the bottle. The signal detected in the detector of the first set thus identifies that a bottle has been loaded which has the groove feature. Therefore, if the user accidentally installed a bottle without the groove or depression feature, the control system would indicate such an occurrence by the absence of the signal in the first emitter and detector set, and would prompt the user to replace the bottle with the correct bottle.

FIGS. 25–28 show how the bottles of FIGS. 2, 7, 12 and 23–24 can be used with a mechanical detection system to distinguish different types of bottles. Referring now to FIG. 24, two bottles 20 are shown installed on a pair of chemical loading mechanisms having an upper case 102 to receive the bottles. Both bottles have a detection feature in the form of a raised rim 50. The detection system 220 is a mechanical detection system, and uses two reciprocating sensor probes 222 that move relative to a hall-effect sensor or switch 224 to detect the rim 50. The sensor probes 222 are biased by a spring 226 extending between a fixed stop 228 and a flange 230 on the surface of the probe 222. The probes reciprocate within a fixed mounting slide 232 inside a housing 234. The flange 230 is made from an appropriate material such that it functions as a trigger for the hall effect sensor 224, depending on the position of the flange 230 relative to the sensor 224.

As is shown in more detail in FIG. 29, the hall-effect sensor 224 includes three separate hall-effect sensors adjacent to each other. A first lateral sensor 236 is for when the probe 222 and trigger flange is in an extended position (bottle with groove), a middle sensor 238 for when the probe 222 is in a middle position (when a bottle is installed which has no rim or groove), and a third or inner sensor 240 for when the probe is in a retracted position (bottle with rim installed).

The tip of the probe 222 is pushed by the bottle side wall when the bottle is installed on the opening structure in the chemical loading system. When the bottle is filly seated, the probe is immediately opposite the rim (or groove) detection feature 50 on the side of the bottle. The probe assumes a position against the force of the spring depending on whether the bottle has a groove, rim, or no feature. This position will place the trigger flange 230 next to one of the three hall-effect sensors 236, 238 and 240, resulting in a signal being sent to the control system of the dialysis machine indicating the configuration of the bottle that is installed in the machine.

Figure 25:
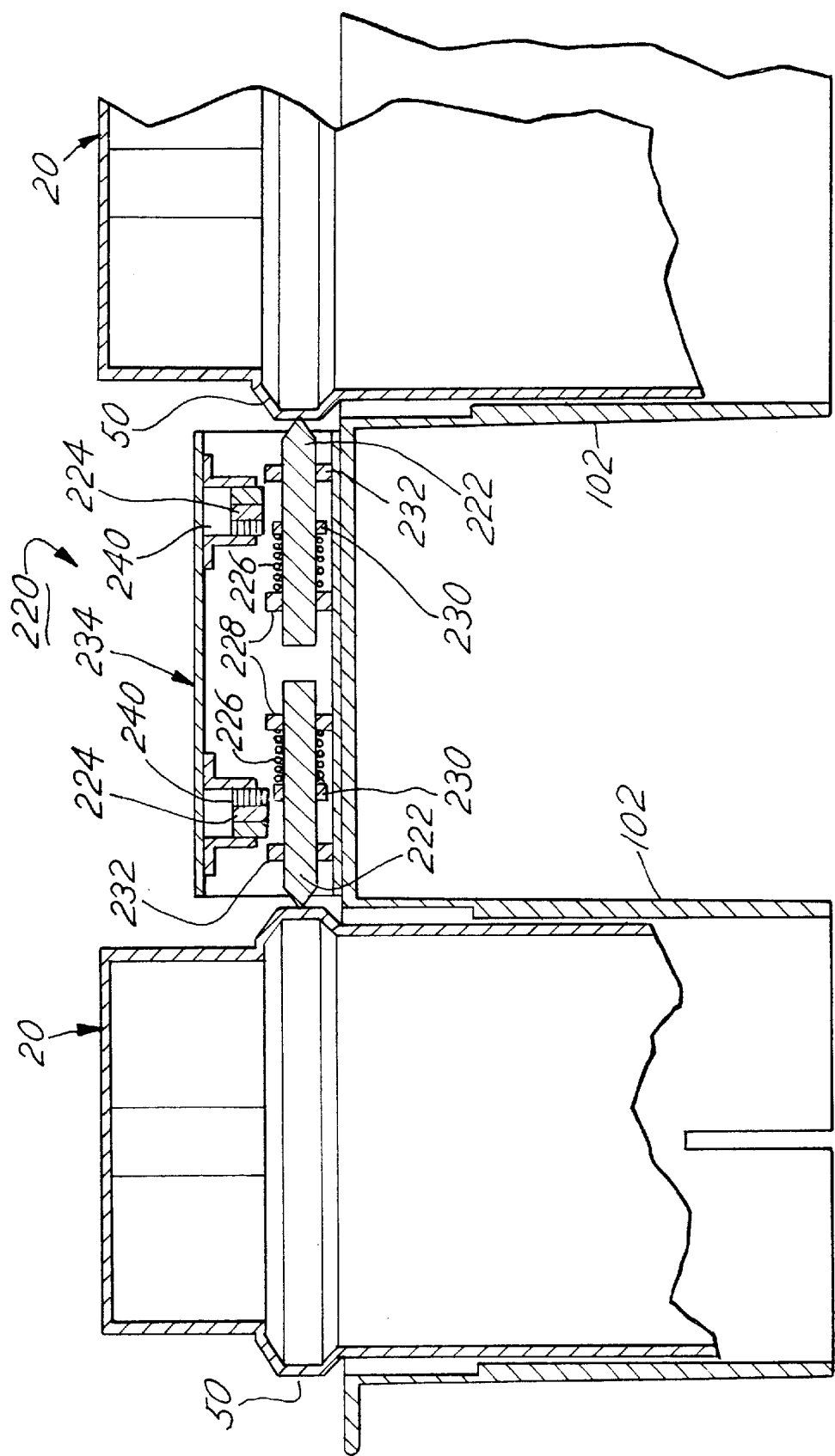
FIG. 25 is an illustration of a portion of a chemical loading system comprising two bottle opening mechanisms of the type shown in FIG. 14, showing two bottles installed which have a detection feature in the form of a raised rim (such as shown in FIGS. 2 and 7) and showing a mechanical detection system detecting the raised rim of the bottles by virtue of movement of a sensor probe in the detection system to a retracted position.

As shown in FIG. 25, when a bottle 20 is installed having a raised rim feature, the probe 222 is pushed to a retracted position, resulting in the flange 230 being placed adjacent to and triggering of the inner hall effect sensor 240 of FIG. 29.

Figure 26:
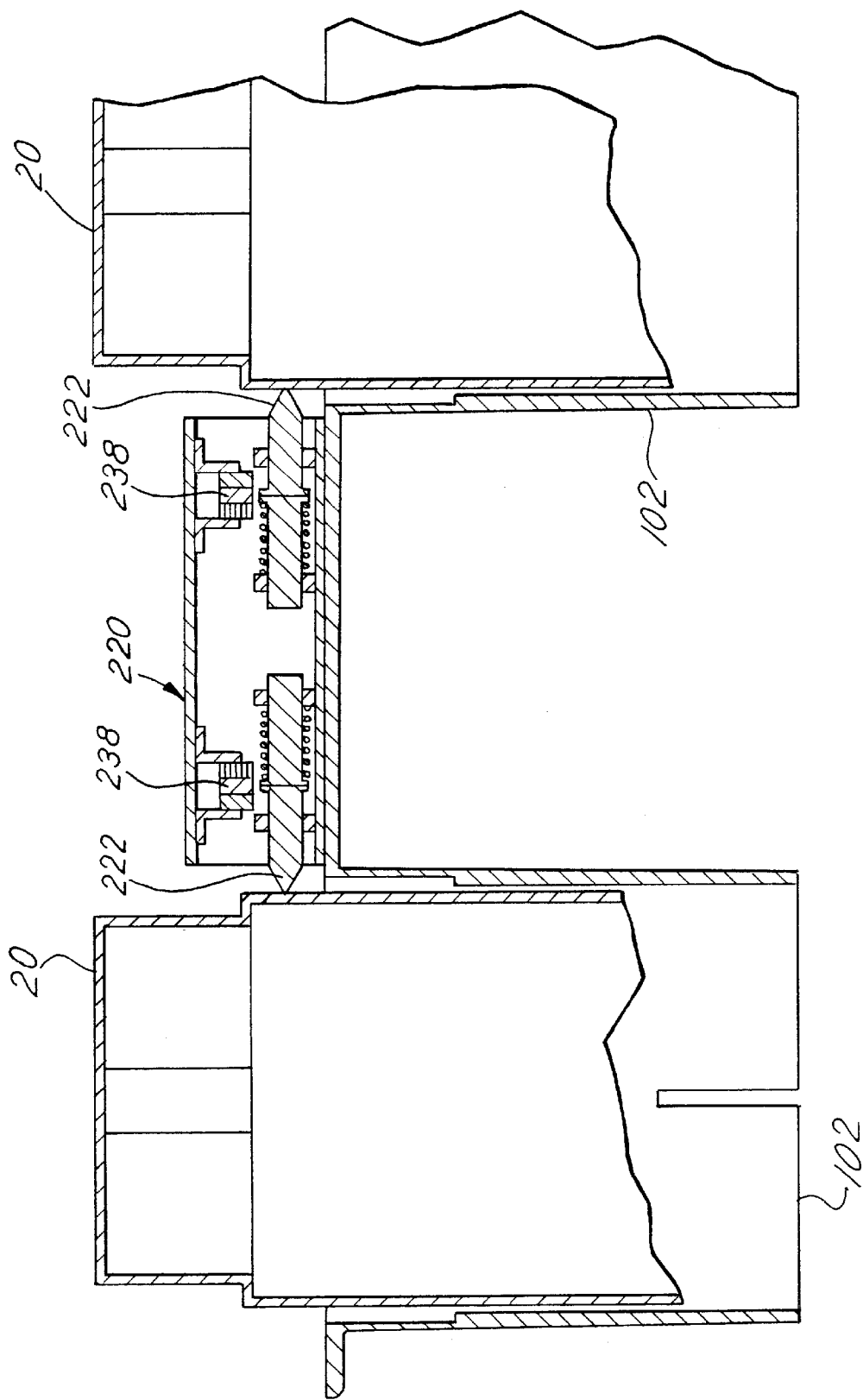
FIG. 26 is an illustration of a portion of the chemical loading system of FIG. 25, showing two bottles installed which have no rim detection feature (i.e., the bottle sidewall is smooth in the region of interest), with the detection system detecting the smooth sidewall by virtue of the movement of the sensor probe to an intermediate position.
Figure 27:
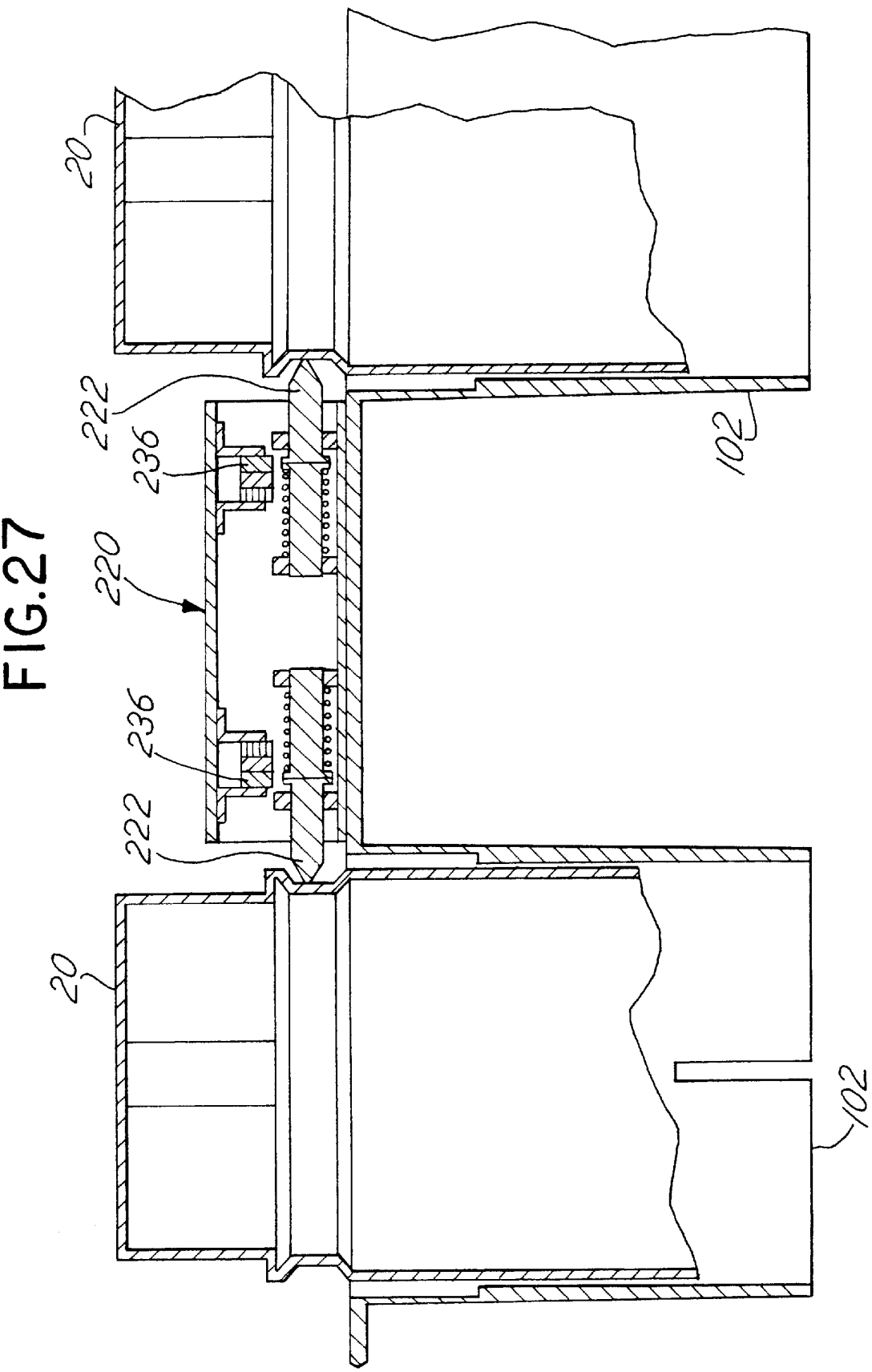
FIG. 27 is an illustration of a portion of the chemical loading system of FIG. 25, showing two bottles installed which have a detection feature in the form of a groove (such as shown in FIGS. 23 and 24), with the sensor probe moving to an extended position to detect the groove.

As shown in FIG. 26, when a bottle is installed having a straight sidewall (no raised rim or groove) the probe is located at a position where sensor 238 is triggered. As shown in FIG. 27, when a bottle is installed which has a groove, hall-effect sensor 236 is triggered. When no bottle is installed, the probe 222 takes the position shown in FIG. 28, with the trigger flange 230 located below hall-effect sensor 236. Alternatively, when no bottle is present the trigger flange 230 could be positioned laterally with respect to the hall-effect sensor 236, such that none of the hall-effect sensors generate a signal when no bottle is installed.

Four possible positions of the sensor probe 222 can be used in any combination of two bottles to differential bottles with different purposes. These four positions are bottle with projecting rim, bottle with indented groove, straight wall bottle, and no bottle present. Also, the two A and B bottles can be used for several special combinations of prescriptions, cleaners and disinfectants, as shown in the following table.

TABLE 1

| Position # | A bottle | B bottle | Used for |
|---|---|---|---|
| 1 | Projected Ring | Projected Ring | Std. Prescription Dialysate |
| 2 | Straight Wall | Straight Wall | Chemical Cleaner Disinfectant |
| 3 | No Bottle | No Bottle | Safety Check |
| 4 | Indented Ring | Indented Ring | Special Prescription Dialysate |
| 5 | Projected Ring | Indented Ring | Special Prescription Dialysate |
| 6 | Indented Ring | Projected Ring | Special Prescription Dialysate |
| 7 | Projected Ring | No Bottle | Safety Check |
| 8 | Indented Ring | No Bottle | Safety Check |
| 9 | No Bottle | Projected Ring | Safety Check |
| 10 | No Bottle | Indented Ring | Safety Check |
| 11 | Straight Wall | No Bottle | Liquid Cleaner/Disinfectant |
| 12 | No Bottle | Straight Wall | Powder Cleaner/Disinfectant |

The designation "safety check" in the table indicates that if the stated condition is present, the machine either alerts the patient to insert a bottle, sounds an alarm, or take other action. If the machine is in a chemical cleaning mode and the hall effect sensors indicate that position 2 is occuring, then the machine goes forward and the bottles are opened. If, however, say position 5 is present, then the machine will activate an alarm or prompt the user to replace the bottles with the proper bottles.

Persons of skill in the art will appreciate that the preferred embodiments are offered by way of illustration and not limitation, and that various modifications and alternative configurations can be made to the chemical loading system, bottles, detection system and other aspects of the preferred and alternative embodiments without departure from the scope of the invention. This true scope and spirit is to be determined by reference to the appended claims.

What is claimed is:

1. Dialysis apparatus comprising:
   a bottle and a detection system for detecting said bottle, said bottle for containing chemicals to be introduced into a dialysis machine, said bottle adapted to be installed on a chemical loading system in said dialysis machine in order to open said bottle and introduce said chemicals into a fluid path in said dialysis machine, the bottle comprising:
   a bottle shell having a sidewall defining a bottle axis, a shoulder portion, a corner portion at which said shoulder portion intersects said sidewall, a lower portion, and a mouth through which said chemicals may be withdrawn from said bottle;
   said bottle further comprising at least one raised rim extending outwardly from said sidewall extending around the circumference of said sidewall in a manner perpendicular to said axis;
   said raised rim positioned on said sidewall a predetermined distance from said corner portion and said mouth such that, when said bottle is installed on said chemical loading system, said rim engages said detection system in said chemical loading system;
   wherein said detection system detects said rim enabling the presence of said bottle to be detected and discriminated from the installation of a bottle without said raised rim.

2. The dialysis apparatus of claim 1, wherein said shoulder portion comprises a frusto-conical wall having a cone angle of between about 35 degrees and about 70 degrees, and a height of between one half and two inches, thereby promoting the release of said chemicals from said bottle.

3. The dialysis apparatus of claim 1, wherein said bottle has an interior surface and wherein a low friction coating is applied to said interior surface to promote release of the contents of said bottle.

4. The dialysis apparatus of claim 1, wherein said mouth has a diameter of between 1 and 2 inches.

5. The dialysis apparatus of claim 1, wherein said rim has a height of between 0.1 and 0.2 inches.

6. The dialysis apparatus of claim 1, wherein said rim has a length measured along said bottle axis of between one half and 1 inches.

7. The dialysis apparatus of claim 1, wherein said bottle is made by a blow-molding process.

8. The dialysis apparatus of claim 1, wherein said lower portion of said bottle further comprises a plurality of flat sides oriented parallel to said bottle axis and arranged around the bottom of said bottle and intersecting one another to thereby promote the gripping of said bottle.

9. The dialysis apparatus of claim 8, wherein each of said flat sides further comprises a plurality of raised features forming a knurled surface on said flat sides.

10. The dialysis apparatus of claim 1, wherein said bottle contains a unit dose of powdered dialysate solution chemicals.

11. The dialysis apparatus of claim 1, wherein said bottle contains a unit dose of liquid acid dialysis solution chemicals.

12. The dialysis apparatus of claim 1, wherein said bottle contains a chemical cleaning solution.

13. The dialysis apparatus of claim 1, wherein the ratio of the width of said mouth to the diameter of said bottle is about 1:2, and wherein the ratio of said width of said mouth to the height of said bottle is between 1:4 and 1:5.

14. The dialysis apparatus of claim 1, wherein bottle further comprises a top portion having (a) a first set of screw threads for receiving a cap for said bottle, said first set positioned adjacent to said mouth, and (b) a second set of screw threads adapted for mounting said bottle to an opening apparatus in a dialysis machine, said second set of screw threads positioned below said first set of screw threads such that said first set of screw threads is between said second set of screw threads and said mouth.

15. The dialysis apparatus of claim 14, wherein said second set of screw threads comprises a set of bayonet screw threads.

16. Dialysis apparatus comprising:
a bottle and a detection system for detecting said bottle,
said bottle for containing chemicals to be introduced into a dialysis machine, said bottle adapted to be installed on a chemical loading system in said dialysis machine in order to open said bottle and introduce said chemicals into a fluid path in said dialysis machine, the bottle comprising:
a bottle shell having a sidewall defining a bottle axis, a shoulder portion, a comer portion at which said shoulder portion intersects said sidewall, a lower portion, and a mouth through which said chemicals may be withdrawn from said bottle;
said bottle further comprising at least one groove extending inwardly from said sidewall extending around the circumference of said sidewall in a manner perpendicular to said axis;
said groove positioned on said sidewall a predetermined distance from said corner portion and said mouth such that, when said bottle is installed on said chemical loading system, said detection system detects said groove enabling the presence of said bottle to be detected and discriminated from the installation of a bottle without said groove.

17. The dialysis apparatus of claim 16, wherein said shoulder portion comprises a frusto-conical wall having a cone angle of between about 35 degrees and about 70 degrees, and a height of between one half and two inches, thereby promoting the release of said chemicals from said bottle.

18. The dialysis apparatus of claim 16, wherein said bottle has an interior surface and wherein a low friction coating is applied to said interior surface to promote release of the contents of said bottle.

19. The dialysis apparatus of claim 16, wherein said mouth has a diameter of between 1 and 2 inches.

20. The dialysis apparatus of claim 16, wherein said bottle is made by a blow-molding process.

21. The dialysis apparatus of claim 16, wherein said lower portion of said bottle further comprises a plurality of flat sides oriented parallel to said bottle axis and arranged around the bottom of said bottle and intersecting one another to thereby promote the gripping of said bottle.

22. The dialysis apparatus of claim 21, wherein each of said flat sides further comprises a plurality of raised features forming a knurled surface on said flat sides.

23. The dialysis apparatus of claim 16, wherein said bottle contains a unit dose of powdered dialysate solution chemicals.

24. The dialysis apparatus of claim 16, wherein said bottle contains a unit dose of liquid acid dialysis solution chemicals.

25. The dialysis apparatus of claim 16, wherein said bottle contains a chemical cleaning solution.

26. The dialysis apparatus of claim 16, wherein the ratio of the width of said mouth to the diameter of said bottle is about 1:2, and wherein the ratio of said width of said mouth to the height of said bottle is between 1:4 and 1:5.

27. The dialysis apparatus of claim 16, wherein bottle further comprises a top portion having (a) a first set of screw threads for receiving a cap for said bottle, said first set positioned adjacent to said mouth, and (b) a second set of screw threads adapted for mounting said bottle to an opening apparatus in a dialysis machine, said second set of screw threads positioned below said first set of screw threads such that said first set of screw threads is between said second set of screw threads and said mouth.

28. The dialysis apparatus of claim 14, wherein said second set of screw threads comprises a set of bayonet screw threads.

29. Apparatus for use in a dialysis machine comprising:
a chemical loading system and a chemical bottle detection system;
a bottle for containing a dialysate chemical formulation, said bottle adapted to be installed on said chemical loading system in order to open said bottle and introduce said dialysate chemical formulation into a fluid path in said dialysis machine, the bottle comprising:
a bottle shell having a sidewall defining a bottle axis, a shoulder portion, a comer portion at which said shoulder portion intersects said sidewall, a lower portion, and a mouth through which said chemicals may be withdrawn from said bottle;
said bottle further comprising a detection feature comprising either a raised rim or a groove extending either outwardly or inwardly from said sidewall, respectively, and positioned around the circumference of said sidewall in a manner perpendicular to said axis;
said detection feature extending around said sidewall and positioned a predetermined distance from said comer portion and said mouth such that, when said bottle is installed on said chemical loading system, said detection feature engages said detection system in said chemical loading system thereby detecting the presence of said bottle and discriminating between a bottle not having said detection feature;
wherein said shoulder portion comprises a frusto-conical wall having a cone angle of at least about 60 degrees;
wherein said mouth has a diameter of between 1 and 2 inches; and wherein
said bottle further comprises a cylindrical top portion having comprising a set of bayonet screw threads adapted for mounting said bottle to said chemical loading system.

30. The apparatus of claim 29, wherein said rim has a length measured along said bottle axis of at least ¼ inch.

31. The apparatus of claim 29, wherein said bottle is made by a blow-molding process.

32. The apparatus of claim 29, wherein said bottle has an interior surface and wherein a low friction coating is applied to said interior surface to promote release of said dialysate chemical formulation.

33. The apparatus of claim 29, wherein said frusto-conical wall has a height of between 1½ and 2 inches.

34. Apparatus for use in a dialysis machine comprising:
a chemical loading system and a chemical bottle detection system;
a bottle for containing a dialysate chemical formulation, said bottle adapted to be installed on said chemical loading system in a dialysis machine in order to open said bottle and introduce said dialysate chemical formulation into a fluid path in said dialysis machine, the bottle comprising:
a bottle shell having a sidewall defining a first axis, a shoulder portion, a corner portion at which said shoulder portion intersects said sidewall, a lower portion, and a mouth through which said chemicals may be withdrawn from said bottle;

said bottle further comprising a detection feature comprising either a raised rim or a groove extending either outwardly or inwardly from said sidewall, respectively, and positioned around the circumference of said sidewall in a manner perpendicular to said axis;

said detection feature extending around said sidewall and positioned a predetermined distance from said corner portion and said mouth such that, when said bottle is installed on said chemical loading system, said detection feature engages said detection system in said chemical loading system thereby detecting the presence of said bottle and discriminating between a bottle not having said detection feature;

wherein said shoulder portion comprises a frusto-conical wall having a cone angle of between about 30 degrees and about 40 degrees;

wherein said mouth has a diameter of between 1 and 2 inches; and wherein said neck portion comprises a set of bayonet screw threads adapted for mounting said bottle to said chemical loading system.

35. The apparatus of claim 34, wherein said detection feature has a length measured along said bottle axis of at least ¼ inch.

36. The apparatus of claim 34, wherein said bottle is made by a blow-molding process.

37. The apparatus of claim 34, wherein said bottle has an interior surface and wherein a low friction coating is applied to said interior surface to promote release of said dialysate chemical formulation.

38. The apparatus of claim 34, wherein said frusto-conical wall has a height of between ½ and 1 inch.

39. The apparatus of claim 34, wherein said bottle contains a liquid acid dialysate chemical formulation.

40. A kit for preparation of a batch of dialysate solution in a dialysis machine, comprising:
a bicarbonate formulation contained in a first batch chemical vessel;
a liquid acid formulation contained in a second batch chemical vessel;
said first and second batch chemical vessels comprising a sidewall defining a first axis, a shoulder portion, a corner portion at which said shoulder portion intersects said sidewall, a lower portion, and a mouth through which said chemicals may be withdrawn from said bottle;
and wherein said shoulder portion of said first batch chemical vessel comprises a frusto-conical wall having a first cone angle and a first height, and wherein said mouth of said first batch chemical vessel is a first diameter; and
wherein said shoulder portion of said second batch chemical vessel comprises a frusto-conical wall having a second cone angle different from said first cone angle and a second height different from said first height, and wherein said mouth of said second batch chemical vessel is a second diameter different from said first diameter;
and wherein said differences in at least one of said cone angle, frusto-conical wall height, and mouth diameter between said first and second bottles cooperate with a first bottle mounting structure and a second bottle mounting structure adapted to receive said first and second bottles, respectively, in said dialysis machine to thereby prevent said first and second bottles from being inadvertently installed on the second and first bottle mounting structures, respectively.

41. The kit of claim 40, further comprising:
a chemical cleaning agent contained in a third batch chemical vessel having a sidewall, shoulder portion and a mouth, said third batch chemical vessel being substantially identical in shape to one of said first and second batch chemical vessels, said third batch chemical vessel further comprises a dectection feature comprising either a raised rim or a groove extending circumferentially around the periphery of said sidewall a predetermined distance from said mouth.

42. The kit of claim 40, further comprising:
a chemical cleaning agent contained in a third batch chemical vessel having a sidewall, shoulder portion and a mouth, said third batch chemical vessel being substantially identical in shape to one of said first and second batch chemical vessels, wherein said first and said second batch chemical vessels further comprise a detection feature comprising either a raised rim or a groove extending circumferentially around the periphery of said sidewall a predetermined distance from said mouth, and said third batch chemical vessel lacks said detection feature provided in said first and second batch chemical vessels enabling said third batch chemical vessel to be distinguished from said first and second batch chemical vessels.

43. A chemical loading system for a dialysis machine, adapted for receiving a first bottle and a second bottle, said first and second bottles containing batch quantity chemicals to be introduced into said machine,
said first and second bottles comprising a sidewall defining a bottle axis, a shoulder portion, a corner portion at which said shoulder portion intersects said sidewall, a lower portion, and a mouth through which said chemicals may be withdrawn from said bottle, said bottles further comprising a detection feature comprising either a raised rim extending outwardly from said sidewall extending around the circumference of said sidewall in a manner perpendicular to said axis, or a groove extending inwardly from said sidewall extending around the circumference of said sidewall in a manner perpendicular to said axis, said detection feature positioned a predetermined distance from said corner portion and said mouth;
the chemical loading system comprising:
(a) a first chemical loading mechanism and a second chemical loading mechanism,
(b) said first chemical loading mechanism adapted to receive said first bottle and said second chemical loading system adapted to receive said second bottle and wherein said first and second bottles and said first and second chemical loading mechanisms are configured such that said first chemical loading mechanism will not receive said second bottle and said second chemical loading mechanism will not receive said first bottle; and
(c) wherein said first and second chemical loading mechanisms further comprise a detection system for detecting said detection feature provided in said first and second chemical bottles, said detection system operative such that when said first and second bottles are installed on said first and second chemical loading mechanisms, said detection feature engages said detection system enabling the presence of said bottles to be detected and discriminated from the installation of a bottle without said detection feature.

44. The chemical loading system of claim 43, wherein said detection system comprises a mechanical detection system.

45. The chemical loading system of claim 43, wherein said detection system comprises an optical detection system.

46. The chemical loading system of claim 43, wherein said detection system comprises a first optical transmitter and a first optical receiver, and a second optical transmitter and a second optical receiver, wherein said first optical transmitter and receiver are positioned relative to said first and second chemical loading mechanisms to detect the installation of a bottle on said chemical loading mechanisms, and wherein said second optical transmitter and second optical receiver are positioned relative to said chemical loading mechanisms to detect said detection feature located on said first and second bottles.

47. The chemical loading system of claim 43, wherein said first bottle contains a powdered bicarbonate formulation and wherein said first chemical loading system further comprises a dissolution chamber positioned in registry with said bottle, a knife for opening said first bottle, and a fluid conduit connecting said dissolution chamber to a dialysate preparation tank in said machine.

48. The chemical loading system of claim 43, wherein said detection system comprises a probe moveable between at least a first position and a second position, said probe actuated by movement of said detection feature on said first and second bottles past said mechanical detection system as said first and second bottles are installed on said chemical loading system.

49. The chemical loading system of claim 48, wherein said detection system further comprises a Hall-effect sensor cooperating with said probe to provide a signal indicating the presence of a detection feature in said first and second bottles.

50. A method for discriminating between a first type of chemical bottle and a second type of chemical bottle, said first and second types of chemical bottles for installation on a batch dialysate preparation system of a dialysis machine, comprising the steps of:

provided a first physical configuration comprising a detection feature on the periphery of said first type of chemical bottle;

providing a second physical configuration comprising a detection feature on the periphery of said second type of chemical bottle, said second configuration different from said first configuration;

placing a detection system for detecting said first and second physical configurations in a chemical loading system for said dialysis machine;

installing one or more of said first and second types of bottles on said chemical loading system;

detecting, with said detection system, said detection features on the bottles installed on said chemical loading system, and determining from said step of detecting the type of bottles installed on said chemical loading system.

51. The method of claim 50, wherein said first physical configuration comprises a circumferential raised rim extending around the circumference of said first type of bottle and wherein said second physical configuration comprises a smooth sidewall extending around the circumference of said second chemical bottle at an elevation of where said circumferential raised rim is provided on said first type of bottle.

52. The method of claim 50, wherein said first physical configuration comprises a circumferential groove extending around the circumference of said first type of bottle and wherein said second physical configuration comprises a smooth sidewall extending around the circumference of said second chemical bottle at an elevation of where said circumferential groove is provided on said first type of bottle.

* * * * *